US 7,967,743 B2

(12) United States Patent
Ishihara

(10) Patent No.: US 7,967,743 B2
(45) Date of Patent: Jun. 28, 2011

(54) ENDOSCOPE OBSERVATION DEVICE, OBSERVATION DEVICE AND OBSERVATION METHOD USING ENDOSCOPE

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 1139 days.

(21) Appl. No.: 11/707,204

(22) Filed: Feb. 15, 2007

(65) Prior Publication Data

US 2007/0197874 A1    Aug. 23, 2007

(30) Foreign Application Priority Data

Feb. 23, 2006 (JP) .................................. 2006-046639

(51) Int. Cl.
*A61B 1/00* (2006.01)
*A61B 1/04* (2006.01)
(52) U.S. Cl. ...................... 600/103; 600/117; 600/118
(58) Field of Classification Search .................. 600/117, 600/160, 180; 356/456, 482, 496, 498
See application file for complete search history.

(56) References Cited

U.S. PATENT DOCUMENTS

| | | | | |
|---|---|---|---|---|
| 5,434,669 | A * | 7/1995 | Tabata et al. ................... | 356/477 |
| 6,134,003 | A | 10/2000 | Tearney et al. | |
| 6,485,413 | B1 * | 11/2002 | Boppart et al. ............... | 600/160 |
| 6,668,185 | B2 * | 12/2003 | Toida ............................ | 600/425 |
| 2002/0013512 | A1 * | 1/2002 | Sendai et al. .................. | 600/160 |
| 2004/0181148 | A1 * | 9/2004 | Uchiyama et al. ............ | 600/425 |
| 2005/0018202 | A1 | 1/2005 | Wang | |
| 2005/0168751 | A1 | 8/2005 | Horii et al. | |
| 2005/0203343 | A1 * | 9/2005 | Kang et al. .................... | 600/160 |
| 2006/0192975 | A1 * | 8/2006 | Sato et al. ..................... | 356/497 |
| 2007/0076217 | A1 * | 4/2007 | Baker et al. ................... | 356/498 |

FOREIGN PATENT DOCUMENTS

| | | |
|---|---|---|
| EP | 0 389 453 A1 | 9/1990 |
| GB | 2 355 310 A | 4/2001 |
| JP | 9-294708 | 11/1997 |
| JP | 10-243920 | 9/1998 |
| JP | 11-148897 | 6/1999 |
| JP | 2002-65581 | 3/2002 |

OTHER PUBLICATIONS

European Office Action dated Sep. 17, 2010.
Sandoz, P., et al., "Profilometry by zero-order interference fringe identification", Journal of Modern Optics, 1993, vol. 40, No. 9, 1691-1700.
Extended European Search Report dated Nov. 22, 2010.

* cited by examiner

*Primary Examiner* — Philip R Smith
(74) *Attorney, Agent, or Firm* — Scully, Scott, Murphy & Presser, P.C.

(57) ABSTRACT

A high accurate image of a specimen is obtained by accurately measuring a distance between the specimen and a tip of a light emitting portion that irradiates a light to the specimen. An endoscope observation device includes the light emitting portion that irradiates the light to the specimen and a light receiving portion that receives an observation light returning from the specimen so as to form an image of the observation light received by the light receiving portion. The endoscope observation device is equipped with a distance measurement unit that measures an absolute distance between the tip of the insertion portion and the specimen through an interference of the low coherence light, a correction unit that corrects the brightness information of the observation light based on the absolute distance measured by the distance measurement unit, and an image forming unit that forms the image of the specimen based on the brightness information of the observation light corrected by the correction unit.

20 Claims, 14 Drawing Sheets

ENDOSCOPE OBSERVATION DEVICE, OBSERVATION DEVICE AND OBSERVATION METHOD USING ENDOSCOPE

BACKGROUND OF THE INVENTION

1. Field of the Invention

The invention relates to an endoscope observation device, an observation device and an observation method using the endoscope.

This application is based on Japanese Patent Application No. 2006-046639, the content of which is incorporated herein by reference.

2. Description of Related Art

Generally, a fluorescent endoscope system for observing the fluorescence generated by irradiating the excitation light to a live body tissue has been disclosed by Japanese Unexamined Patent Application, Publication No. 10-243920 (hereinafter referred to as Patent Document 1), for example.

The aforementioned fluorescent endoscope system is structured to irradiate the excitation light to a live body, and to detect the fluorescence naturally emitted from the live body or the fluorescence from the medicine which has been infused to the live body in the form of two-dimensional images. The fluorescent endoscope system allows the diagnosis of the disease, for example, degeneration of the body tissue or cancer based on the detected fluorescent image.

In order to accurately detect the degree of malignant of the cancer cell and the like, the absolute value of the quantity of the fluorescence emitted by the body tissue has to be accurately obtained. The quantity of the fluorescence received by a light receiving portion disposed at a tip of an insertion portion varies as the distance between the tip of the insertion portion and a specimen such as the body tissue. It is therefore indispensable to establish the process for obtaining the absolute value of the fluorescent quantity irrespective of the fluctuation as described above.

Patent Document 1 discloses the fluorescent endoscope system equipped with a distance measurement unit using ultrasonic signals for measuring the distance between the tip of the insertion portion and the specimen.

Japanese Unexamined Patent Application, Publication No. 11-148897 discloses an optical imaging apparatus using the technique to irradiate the low coherence light to the specimen such that the accurate tomogram of the specimen is obtained from the information of the light scattered in the specimen, that is, OCT (optical coherence tomography) technique.

The distance measurement unit using the ultrasonic wave may work only when the space from the ultrasonic wave oscillator to the specimen is filled with water. It is not capable of measuring the distance of the space filled with air.

The generally employed OCT technique has been used only to form the tomogram of the specimen.

BRIEF SUMMARY OF THE INVENTION

It is an object of the invention to provide an endoscope observation device, the observation device, and the observation method using the endoscope which allow accurate measurement of the distance between a specimen and a tip of the light emitting portion for irradiating the light to the specimen so as to obtain the quantitative image of the specimen irrelevant to the influence of the distance from the specimen.

The invention provides the following means for the purpose of achieving the aforementioned object.

The first aspect of the invention provide an endoscope observation device in which a tip of an insertion portion to be inserted into a body cavity is provided with a light emitting portion that irradiates light rays to a specimen and a light receiving portion that receives an observation light returning from the specimen for forming an image of the observation light received by the light receiving portion. The endoscope observation device is provided with a distance measurement unit that calculates an absolute distance between the tip of the insertion portion and the specimen through an interference of a low coherence light, a correction unit that corrects a piece of brightness information of the observation light based on the absolute distance calculated by the distance measurement unit, and an image forming unit that forms an image of the specimen based on the brightness information of the observation light corrected by the correction unit.

In the first aspect of the invention, the distance measurement unit is operated to measure the absolute distance between the tip of the insertion portion provided with the light emitting portion and the light receiving portion and the specimen using the OCT technique through interference of the low coherence light. Assuming that the light emitting portion uniformly radiates the illuminating light or the excitation light, the brightness of the observation light from the specimen received by the light receiving portion is inversely proportional to the squared absolute distance. Accordingly, the brightness information of the observation light may be accurately corrected by operating the correction unit using the absolute distance accurately measured through the OCT technique.

In the first aspect of the invention, the use of the OCT technique allows arbitrary usage environment unlike the case using the ultrasonic signals to limit the usage environment. This makes it possible to accurately measure the absolute distance in the space filled with air or the biological fluid.

The image forming unit is operated to form the image of the specimen based on the corrected brightness information such that the image with the accurate brightness distribution is obtained irrelevant to the distance between the tip of the insertion portion and the specimen.

The first aspect of the invention may be structured that the insertion portion includes a base light split unit that is fixed in the insertion portion for splitting the low coherence light into a base light and a measurement light and for guiding the measurement light to the specimen, and the distance measurement unit includes a distance calculation unit that calculates the absolute distance between the tip of the insertion portion and the specimen based on a difference between an optical path length from the base light split unit and the specimen measured using at least the base light and the measurement light returning from the specimen as an interference light and an optical path length from the base light split unit and the tip of the insertion portion.

The low coherence light is split into the base light and the measurement light by the base light split unit fixed within the insertion portion. The measurement light is guided to the specimen. The measurement light that returns after reflecting or scattering on the specimen, and the base light which has been split by the base light split unit may be used as the interference light to obtain the optical path length between the base light split unit and the specimen. As the base light split unit is fixed within the insertion portion, the distance between the base light split unit and the tip of the insertion portion is known. The distance calculation unit obtains the difference in those known values to calculate the absolute distance between the tip of the insertion portion and the specimen accurately. For the interference purpose, the measurement light and the base light may be used not only for the interference therebetween but also for the interference of the other low coherence light with the measurement light and the reference light, respectively.

In the first aspect of the invention, the distance measurement unit includes a low coherence light source, a reference light split unit that splits the reference light from the low coherence light emitted from the low coherence light source, and guides a rest of the low coherence light to the insertion portion, an optical path length adjustment unit that adjusts an optical path length of the reference light split by the reference light split unit, and an optical coupler that combines the measurement light and the base light returning from the specimen with the reference light returning from the optical path length adjustment unit to cause an interference. The distance calculation unit calculates the absolute distance between the tip of the insertion portion and the specimen based on a value obtained by subtracting the optical path length from the base light split unit to the tip of the insertion portion from a difference between a first optical path length of the reference light at a time point when the interference of the measurement light with the reference light occurs in the optical coupler and a second optical path length of the reference light at a time point when the interference of the base light with the reference light occurs in the optical coupler.

The low coherence light emitted from the low coherence light source is split into the measurement light and the reference light by the reference light split unit, and the measurement light is irradiated to the specimen. The measurement light irradiated to the specimen returns after reflecting or scattering on the specimen. Meanwhile, the optical path length adjustment unit adjusts the optical path length of the reference light. The measurement light and the reference light are then combined in the optical coupler. The interference occurs when values of the optical path length from the split performed by the light split unit to the combination coincide accurately.

In this case, part of the measurement light is split by the reference light split unit fixed within the insertion portion and returns as the base light. It is then combined with the reference light in the optical coupler. The interference occurs when the optical path lengths of the base light and the reference light coincide with each other.

In the first aspect of the invention, the absolute distance between the tip surface of the insertion portion and the specimen is accurately calculated by the distance calculation unit based on the value obtained by subtracting the optical path length between the base light split unit and the tip of the insertion portion from the difference between the first optical path length upon interference of the measurement light returning from the specimen with the reference light and the second optical path length upon interference of the base light with the reference light. Based on the calculated absolute distance, the brightness information of the observation light may be accurately corrected. This makes it possible to obtain the image with accurate brightness distribution irrespective to the distance between the tip of the insertion portion and the specimen.

In the first aspect of the invention, the distance measurement unit includes a low coherence light source, an interference light split unit that splits the measurement light and the base light returning from the specimen into two interference optical paths, an optical path length difference adjustment unit that adjusts an optical path length difference between the two interference optical paths, and an optical coupler that combines the low coherence lights each passing through the two interference light paths to cause the interference. The distance calculation unit calculates the absolute distance between the tip of the insertion portion and the specimen based on a value obtained by subtracting an optical path length from the base light split unit to the tip of the insertion portion from the optical path length difference between the two interference optical paths at a time point when an interference between the measurement light and the base light occurs in the optical coupler.

The low coherence light emitted from the low coherence light source is split into the measurement light and the base light in the insertion portion. The measurement light is radiated from the tip of the insertion portion and reflects or scatters on the surface of the specimen. It then returns to the insertion portion together with the base light and further split into two interference optical paths by the interference light split unit. As a result, the measurement light and the base light are expected to pass through the interference optical paths each having the different length.

As the optical path length difference adjustment unit is operated to adjust the difference in the optical path length between those two interference optical paths, the interference occurs in the optical coupler when the difference in the optical path length of the two interference optical paths coincides with the difference in the optical path length between the measurement light and the base light. Accordingly, the distance calculation unit is capable of calculating the absolute distance between the tip of the insertion portion and the specimen based on the value obtained by subtracting the optical path length between the base light split unit and the tip of the insertion portion from the difference in the optical path length between those two interference optical paths during the interference.

In the first aspect, the insertion portion includes a base light split unit fixed to a tip of the insertion portion for splitting the low coherence light into a base light and a measurement light for irradiating the measurement light to the specimen and receiving the measurement light returning from the specimen. The distance measurement unit includes a distance calculation unit that calculates the absolute distance between the tip of the insertion portion and the specimen based on an optical path length from the base light split unit to the specimen, which is calculated using at least the base light and the measurement light reflecting on the specimen as an interference light.

The base light and the measurement light obtained through splitting by the base light split unit as the low coherence lights each having the different optical path length is used to cause the interference. This makes it possible to measure the optical path length between the base light split unit and the specimen accurately. The distance calculation unit is capable of accurately calculating the absolute value of the distance between the tip of the insertion portion and the specimen based only on the measured optical path length. The measurement light and the base light may be used not only for the interference therebetween but also for the interference of the other low coherence light with the measurement light and the base light, respectively for the interference purpose.

In the first aspect of the invention, the distance measurement unit includes a low coherence light source, a reference light split unit that splits a low coherence light emitted from the low coherence light source into a reference light and guides a rest of the coherence light to the insertion portion, an optical path length adjustment unit that adjusts an optical path length of the reference light split by the reference light split unit, and an optical coupler that combines the measurement light and the base light returning from the insertion portion with the reference light returning from the optical path length adjustment unit to cause an interference. The distance calculation unit calculates the absolute distance between the tip of the insertion portion and the specimen based on a difference between a first optical path length of the reference light at a time point when the measurement light interferes with the reference light in the optical coupler, and a second optical path length of the reference light at a time point when the base light is interfered with the reference light in the optical coupler.

The low coherence light emitted from the low coherence light source is split into the measurement light and the reference light by the reference light split unit. The measurement light is then irradiated to the specimen. The measurement light irradiated to the specimen reflects or scatters on the specimens and returns. Meanwhile, the optical path length adjustment unit adjusts the optical path length of the reference light. The measurement light and the reference light are combined in the light coupler. The interference occurs when the optical path lengths from splitting performed by the light split unit to combination coincide with each other accurately.

In this case, part of the measurement light is split by the base light split unit fixed within the insertion portion and returns as the base light, which will be combined with the reference light in the optical coupler. Accordingly, when the optical path length of the base light coincides with that of the reference light accurately, the interference also occurs.

In the first aspect of the invention, the distance calculation unit is operated to accurately calculate the absolute distance between the tip surface of the insertion portion and the specimen based on the difference between the first optical path length upon interference of the measurement light returning from the specimen with the reference light and the second optical path length upon interference of the base light with the reference light. As a result, the brightness information of the observation light may be accurately corrected based on the calculated absolute distance. This makes it possible to obtain the image with the accurate brightness distribution irrespective of the distance between the tip of the insertion portion and the specimen.

In the first aspect of the invention, the distance measurement unit includes a low coherence light source, a reference light split unit disposed inside the insertion portion for splitting a low coherence light emitted from the low coherence light source into a reference light, and guiding a rest of the low coherence light to the tip of the insertion portion, an interference light split unit that splits the measurement light, the base light and the reference light into two respective interference optical paths, an optical path length difference adjustment unit that adjusts an optical path length difference between the two interference optical paths, and an optical coupler that combines the low coherence light passing through the two interference optical paths to cause the interference. The distance calculation unit calculates the absolute distance between the tip end of the insertion portion and the specimen based on a difference between the first optical path length difference between the two interference optical paths at a time point when the measurement light interferes with the reference light in the optical coupler, and a second optical path length difference between the two interference paths at a time point when the base light interferes with the reference light in the optical coupler.

The low coherence light emitted from the low coherence light source is split into the measurement light, the base light and the reference light in the insertion portion. The measurement light is radiated from the tip of the insertion portion and reflected on the surface of the specimen. It then returns to the insertion portion together with the base light and the reference light, and split into two interference optical paths by the interference light split unit. As a result, the measurement light, the base light and the reference light are expected to pass through the interference optical paths each having the different length. The optical path length difference adjustment unit is operated to adjust the difference in the length of those two interference optical paths. Accordingly the interference occurs in the optical coupler when the difference in the length between those two optical paths coincides with the difference in the optical path length between the base light and the reference light, and when the difference of the length between those two optical paths coincides with the difference in the optical path length between the measurement light and the reference light. The difference between those two optical path length differences is obtained as the difference in the optical path length between the measurement light and the base light such that the absolute distance from the tip of the insertion portion to the specimen is accurately calculated.

In this case, the reference light split unit within the insertion portion is allowed to easily enhance the intensity of the reference light by setting the reflectance to a greater value. Accordingly, in the case where the intensity of the measurement light that returns after reflecting on the specimen, or the base light split by the base light split unit fixed to the tip of the insertion portion is low, the intensity of the interference light is enhanced by setting the intensity of the reference light so as to improve the distance measurement accuracy.

The reference light split unit is disposed within the insertion portion to set the optical path length to be short in the optical path length difference adjustment unit, thus making the device compact.

In the first aspect of the invention, the distance measurement unit includes an interference light split unit that splits the measurement light and the base light into two respective interference optical paths, an optical path length difference adjustment unit that adjusts an optical path length difference between the two interference optical paths, and an optical coupler that combines the low coherence light passing through the two interference optical paths. The distance calculation unit calculates the absolute distance between the tip of the insertion unit and the specimen based on an optical path length difference between the two interference optical paths at a point when the measurement light interferes with the base light in the optical coupler.

The low coherence light emitted from the low coherence light source is split into the measurement light and the base light at the tip of the insertion portion. The measurement light is radiated from the tip of the insertion portion and reflected on the surface of the specimen. It then returns to the insertion portion together with the base light and split into two interference optical paths by the interference light split unit. Accordingly, the measurement light and the base light are expected to pass through the interference paths each having the different length.

The optical path length difference adjustment unit is operated to adjust the difference in the optical path length between two interference optical paths. When the difference in the optical path length between two interference optical paths coincides with the difference in the optical path length between the measurement light and the base light, the interference occurs in the optical coupler. The distance calculation unit is allowed to accurately calculate the absolute distance between the tip of the insertion portion and the specimen based on the difference in the optical path length between those two interference optical paths during the interference.

In the first aspect of the invention, preferably, the base light split unit is a reflective film provided to a tip of the insertion portion to reflect a part of the measurement light.

This ensures to keep the quantity of the measurement light that reflects on the tip surface of the insertion portion. Accordingly, the peak value of the interference signal generated by the interference with the reference light may be clarified, which allows the position of the tip surface of the insertion portion to be accurately obtained.

In the first aspect of the invention, the optical path length adjustment unit is allowed to include a mirror that reflects the reference light split by the light split unit to return to the optical coupler, and a mirror movement unit that moves the mirror along an optical axis of the reference light.

The mirror movement unit is operated to move the mirror along the optical axis of the reference light to easily adjust the optical path length of the reference light.

In the first aspect of the invention, the optical path length adjustment unit is allowed to include a reference light split unit that splits the reference light into a plurality of lights, the mirrors and the mirror movement units are disposed to each of the reference lights split by the reference light split unit, and ranges for adjusting the optical path lengths of the reference lights by the mirror movement units are different.

This makes it possible to measure the distance between the specimen and the tip of the insertion portion over a wider measurement range which covers the adjustment range of the optical path length without increasing each displacement of the mirrors moved by the respective mirror movement units.

In the first aspect of the invention, ranges for adjusting the optical path lengths of the reference lights by two or more mirror movement units may be sequentially provided.

This makes it possible to measure the absolute distance between the specimen and the tip of the insertion portion with no gap over the wider measurement range.

In the first aspect of the invention, preferably an optical modulator that allows the reference light split by the reference light split unit to be frequency modulated at a different frequency, and a frequency detector that detects a frequency of the light interfered in the optical coupler are provided.

The reference lights split through operation of the optical modulation unit are combined with the measurement light in the optical coupler at different frequencies through the frequency modulation. The frequency of the light that causes the interference in the optical coupler is detected through operation of the frequency detector. This makes it possible to identify the reference light that interferes with the measurement light based on the detected frequency even if all the split reference lights are injected to the optical coupler simultaneously to be combined with the measurement light. As a result, this makes it possible to promptly measure the absolute distance between the specimen and the tip of the insertion portion over the wide measurement range.

In the first aspect of the invention, preferably the insertion portion includes an optical system that guides the observation light and the low coherence light coaxially.

This makes it possible to reduce the diameter of the insertion portion.

In a second aspect of the invention, provided is an observation device that includes a light emitting portion for irradiating a light to a specimen and a light receiving portion that receives an observation light returning from the specimen at its tip for forming an image of the observation light received by the light receiving portion. The observation device is provided with a distance measurement unit that calculates an absolute distance between the tip and the specimen through an interference of a low coherence light, a correction unit that corrects a piece of brightness information of the observation based on the absolute distance measured by the distance measurement unit, and an image forming unit that forms an image of the specimen based on the brightness information of the observation light corrected by the correction unit.

In the second aspect of the invention, the distance measurement unit is operated to measure the absolute distance between the tip of the observation device equipped with a light emitting portion and a light receiving portion and the specimen using the OCT technique through interference of the low coherence light. Assuming that the light emitting portion radiates the illumination light or the excitation light uniformly, the brightness of the observation light emitted from the specimen to be received by the light receiving portion is inversely proportional to the squared absolute distance. Accordingly, the correction unit is operated to correct the brightness information of the observation light accurately using the absolute distance accurately measured through the OCT technique.

In the second aspect of the invention, the use of the OCT technique allows arbitrary usage environment unlike the case using the ultrasonic signals to limit the usage environment. This makes it possible to accurately measure the absolute distance in the space filled with either air or the biological fluid.

The image forming unit is operated to form the image of the specimen based on the corrected brightness information so as to obtain the image that exhibits the accurate brightness distribution irrespective of the distance between the tip of the observation device and the specimen.

In a third aspect of the invention, provided is an observation method using an endoscope for forming an image by irradiating a light to a specimen from a tip of an insertion portion to be inserted into a body cavity, and receiving an observation light returning from the specimen. The method includes a measurement step of measuring an absolute distance between the tip of the insertion portion and the specimen through an interference of a low coherence light, a correction step of correcting a piece of brightness information of the observation light based on the measured absolute distance, and an image forming step of forming an image of the specimen based on the corrected brightness information of the observation light.

In the third aspect of the invention, the specimen is observed by inserting the insertion portion into the body cavity, irradiating the light from the tip to the specimen, receiving the observation light returning from the specimen, and forming the observation image based on the received observation light. In this case, the light quantity of the received observation light varies as the distance between the specimen and the tip of the insertion portion becomes different. In the third aspect of the invention, the absolute distance between the tip of the insertion portion and the specimen is measured in the measurement step, and the brightness information of the observation light is corrected based on the absolute distance in the correction step, and the image of the specimen is formed based on the corrected brightness information in the image forming step. This makes it possible to accurately observe the state of the specimen without changing the brightness of the observation image in spite of the change in the distance between the tip of the insertion portion and the specimen.

In the third aspect of the invention, the measurement step further is allowed to include steps of splitting a reference light from the low coherence light, and guiding a rest of the coherence light to the insertion portion, splitting the low coherence light into a base light and a measurement light at a tip of the insertion portion, irradiating the split measurement light and receiving the measurement light returning from the specimen, adjusting an optical path length of the split reference light, combining the measurement light and the reference light returning from the tip of the insertion portion to cause an interference, and calculating the absolute distance based on a difference between a first optical path length of the reference light at a time point when the interference occurs between the measurement light and the reference light returning from the specimen and a second optical path length of the reference light at a time point when an interference occurs between the base light and the reference light.

The use of the OCT technique allows the first and the second optical path lengths to be determined based on the measurement light that returns from the specimen and the measurement light that returns from the tip surface of the insertion portion. The use of the resultant difference allows easy and accurate measurement of the absolute distance between the tip of the insertion portion and the specimen.

In the third aspect of the invention, the reference light may be split to a plurality of optical paths each having a different optical path length such that each of the split reference lights is subjected to adjustment of the optical path length.

This makes it possible to measure the distance between the specimen and the tip of the insertion portion over the wide measurement range without dividing the range of the optical path length adjustment and enlarging the adjustment range for the respective optical paths.

In the third aspect of the invention, ranges for adjusting the optical path lengths of the split reference lights may be sequentially provided.

This makes it possible to measure the absolute distance between the specimen and the tip of the insertion portion over the wide measurement range with no gap.

In the third aspect of the invention, preferably the split reference lights are frequency modulated to different frequencies such that an optical frequency that causes the interference is detected.

The split reference light is combined with the measurement lights at different frequencies through the frequency modulation. The optical frequency that causes the interference in the optical coupler is detected. This makes it possible to identify the reference light which has interfered with the measurement light based on the detected frequency even if all the split reference lights are simultaneously combined with the measurement light. As a result, the measurement of the absolute distance between the specimen and the tip of the insertion portion may be promptly performed over the wide measurement range.

The invention allows accurate measurement of the distance between the specimen and the tip of the light emitting portion that irradiates the light to the specimen so as to obtain the high accurate image of the specimen.

DETAILED DESCRIPTION OF THE INVENTION

Figure 1:
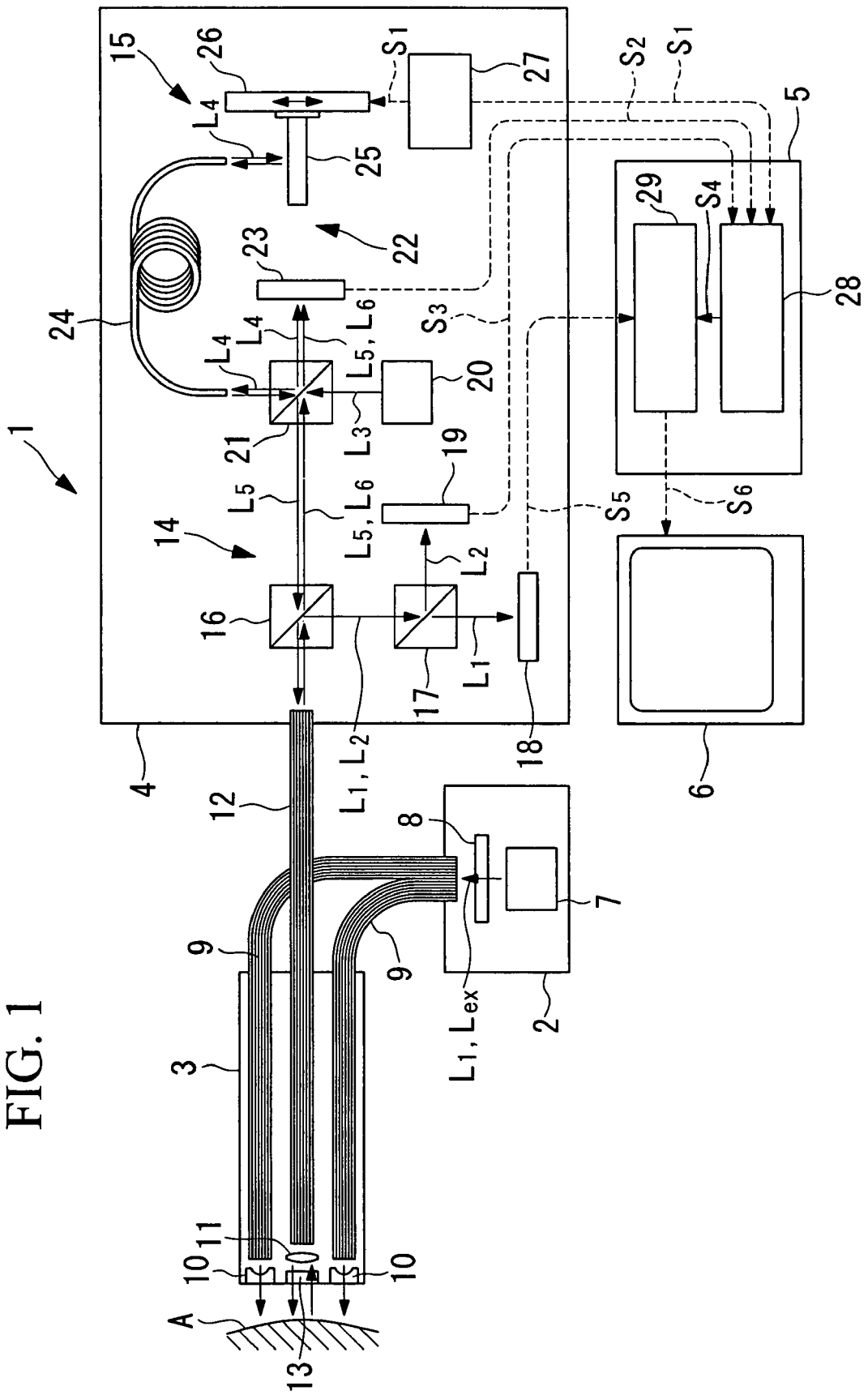
FIG. 1 is a view showing an entire structure of an endoscope observation device according to a first embodiment of the invention.

An endoscope observation device according to a first embodiment of the invention will be described referring to FIGS. 1 to 3.

An endoscope observation device 1 of the embodiment includes a light source unit 2, a long and thin insertion portion 3 connected to the light source unit 2 and inserted into the body cavity, a detection unit 4 connected to the insertion portion 3 to detect the return light from a body tissue A as a specimen, an image processing unit 5 that forms the image of the body tissue A based on a detection signal of the detection unit 4, and an image display unit 6 that displays the image of the body tissue A produced in the image processing unit 5.

Referring to FIG. 1, the light source unit 2 includes a light source 7 that emits the broadband light, for example, a xenon lamp, a halogen lamp and the like, and a filter 8 that allows transmission of white light $L_1$ and excitation light $L_{ex}$ emitted from the light source 7.

The insertion portion 3 includes a light guide (or fiber flux) 9 that guides the light emitted from the light source unit 2 to the tip of the insertion portion 3, a diffusing lens (light emitting portion) 10 disposed at the tip of the insertion portion 3, which diffuses the light propagated through the light guide 9 so as to be irradiated to the opposite body tissue A, an objective lens 11 that converges the light returning from the body tissue A, and an image guide (optical measurement unit) 12 that guides the converged return light to the base end of the insertion portion 3. A reference numeral 13 denotes a cover glass (light receiving portion) disposed at the tip of the image guide 12.

The detection unit 4 includes an image detection unit 14 and a distance measurement unit 15.

The image detection unit 14 includes a first dichroic mirror 16 that splits the reflection light of the white light $L_1$ from the light source unit 2 and the fluorescence $L_2$ generated in the body tissue A among the return light which has been propagated by the image guide 12, a second dichroic mirror 17 that further splits the white light $L_1$ and the fluorescence $L_2$ which have been split by the first dichroic mirror 16, and two pickup elements 18 and 19, for example, the CCD element and the like for detecting the split white light $L_1$ and the fluorescence $L_2$, respectively.

The distance measurement unit 15 includes a low coherence light source 20 that emits the low coherence light $L_3$, a beam splitter (light split unit, optical coupler) 21 that splits the low coherence light $L_3$ emitted from the low coherence light source 20 into the reference light $L_4$ and the measurement light $L_5$, a reference light optical path length adjustment unit (optical path length adjustment unit) 22 that injects the reference light $L_4$ split by the beam splitter 21, and an interference image pickup element 23 such as the CCD element that detects the reference light $L_4$ and the measurement light $L_5$ which return via the beam splitter 21. The pixel of the interference image pickup element 23 is preliminarily correlated with that of those two pickup elements 18 and 19 of the image detection unit 14.

The beam splitter 21 is arranged to split the low coherence light $L_3$ emitted from the low coherence light source 20 such that the reference light $L_4$ is injected to the reference light optical path length adjustment unit 22 and the measurement light $L_5$ is injected to the first dichroic mirror 16, respectively.

The reference light optical path length adjustment unit 22 includes a fiber bundle 24 for the optical path length adjustment to inject the reference light $L_4$ split by the beam splitter 21 from one end, a scanning mirror 25 that reflects the reference light $L_4$ radiated from the other end of the fiber bundle 24 to be returned thereto, a mirror movement mechanism (mirror movement unit) 26 that moves the scanning mirror 25 along the optical axis of the reference light $L_4$, and a mirror controller 27 that controls the mirror movement mechanism 26 to output the position information $S_1$ of the scanning mirror 25.

The measurement light L5 injected to the first dichroic mirror 16 transmits therethrough toward one end of the image guide 12 so as to be injected thereinto. It is further radiated to the body tissue A from the tip of the image guide 12 via the objective lens 11 and the cover glass 13. The measurement light $L_5$ radiated from the tip surface of the cover glass 13 reflects on the surface of the body tissue A and returns into the detection unit 4 via the cover glass 13, the objective lens 11 and the image guide 12. The measurement light $L_5$ returning into the detection unit 4 transmits through the first dichroic mirror 16 and the beam splitter 21 so as to be detected by the interference image pickup element 23.

Meanwhile, the reference light $L_4$ injected to the reference light optical path length adjustment unit 22 is propagated through the fiber bundle 24 and radiated from the other end. It is reflected by the scanning mirror 25 and then returns into the fiber bundle 24. The reference light $L_4$ that returns into the fiber bundle 24 is reflected by the beam splitter 21 and combined with the measurement light $L_5$ so as to be detected by the interference image pickup element 23.

The length of the fiber bundle 24 is set such that the reciprocating optical path length of the reference light $L_4$ in the reference light optical path length adjustment unit 22 becomes substantially equivalent to that of the measurement light $L_5$ from the beam splitter 21 to the body tissue A via the first dichroic mirror 16, the image guide 12, the objective lens 11 and the cover glass 13. The position of the scanning mirror 25 is adjusted such that the interference occurs between the reference light $L_4$ and the measurement light $L_5$ when both reciprocating optical path lengths accurately coincide with each other, and the light intensity detected by the interference image pickup element 23 reaches the peak value. Accordingly, the position of the scanning mirror 25 at which the light intensity detected by the interference image pickup element 23 reaches the peak value is recorded to accurately detect the position of the body tissue A.

Figure 2:
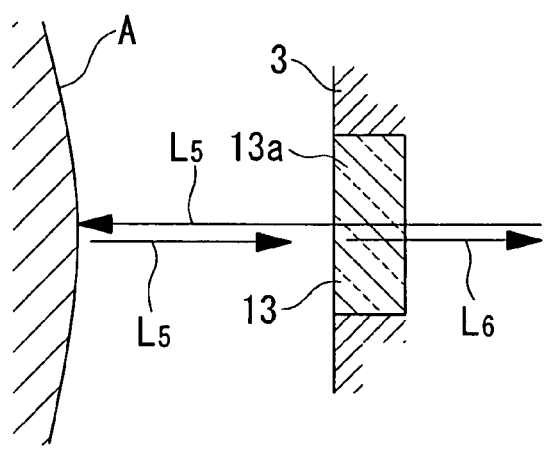
FIG. 2 is a longitudinal sectional view showing a cover glass disposed at a tip of an insertion portion of the endoscope observation device shown in FIG. 1.

In the endoscope observation device 1 according to the embodiment, the cover glass (base light split unit) 13 is attached to the tip of the insertion portion 3 as shown in FIG. 2. The measurement light $L_5$ not only reflects on the surface of the body tissue A to return but also partially reflects on the tip surface 13a of the cover glass 13 to return as the base light $L_6$. Accordingly, the interference image pickup element 23 is structured such that both the measurement light $L_5$ that returns after reflecting on the surface of the body tissue A and the base light $L_6$ that returns after reflecting on the tip surface 13a of the cover glass 13 with the reference light $L_4$, respectively.

Figure 3:
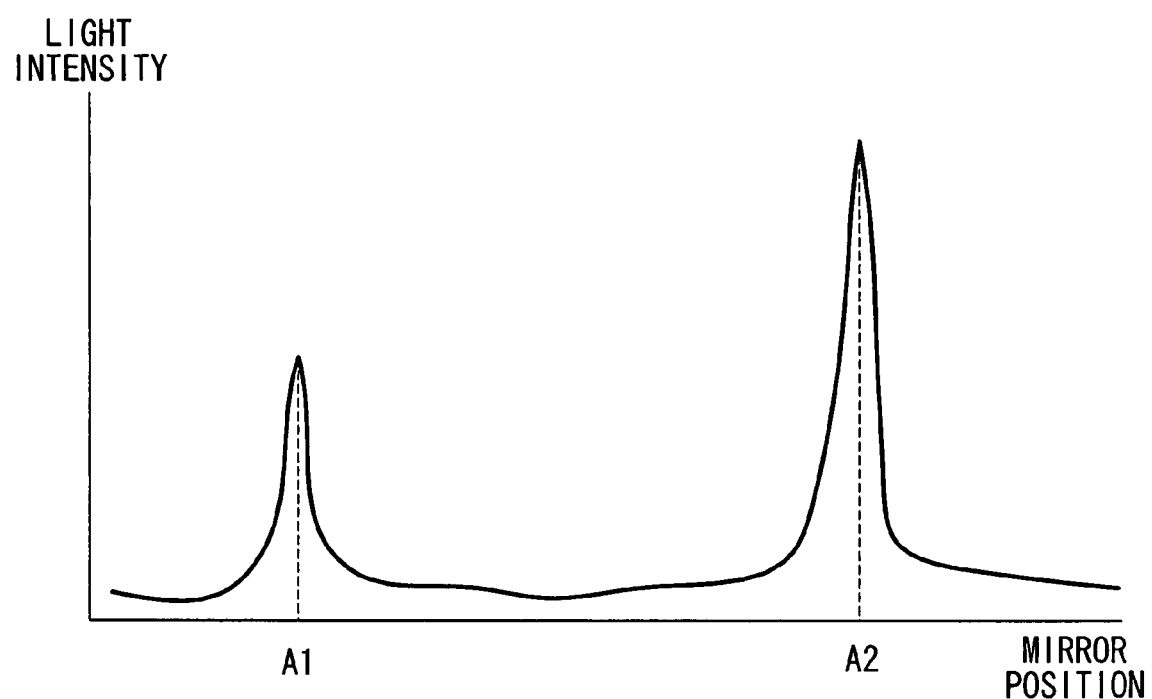
FIG. 3 is a view showing a relationship between the mirror position and the light intensity, which is obtained by the interference image pick-up element of the endoscope observation device shown in FIG. 1.
Figure 4:
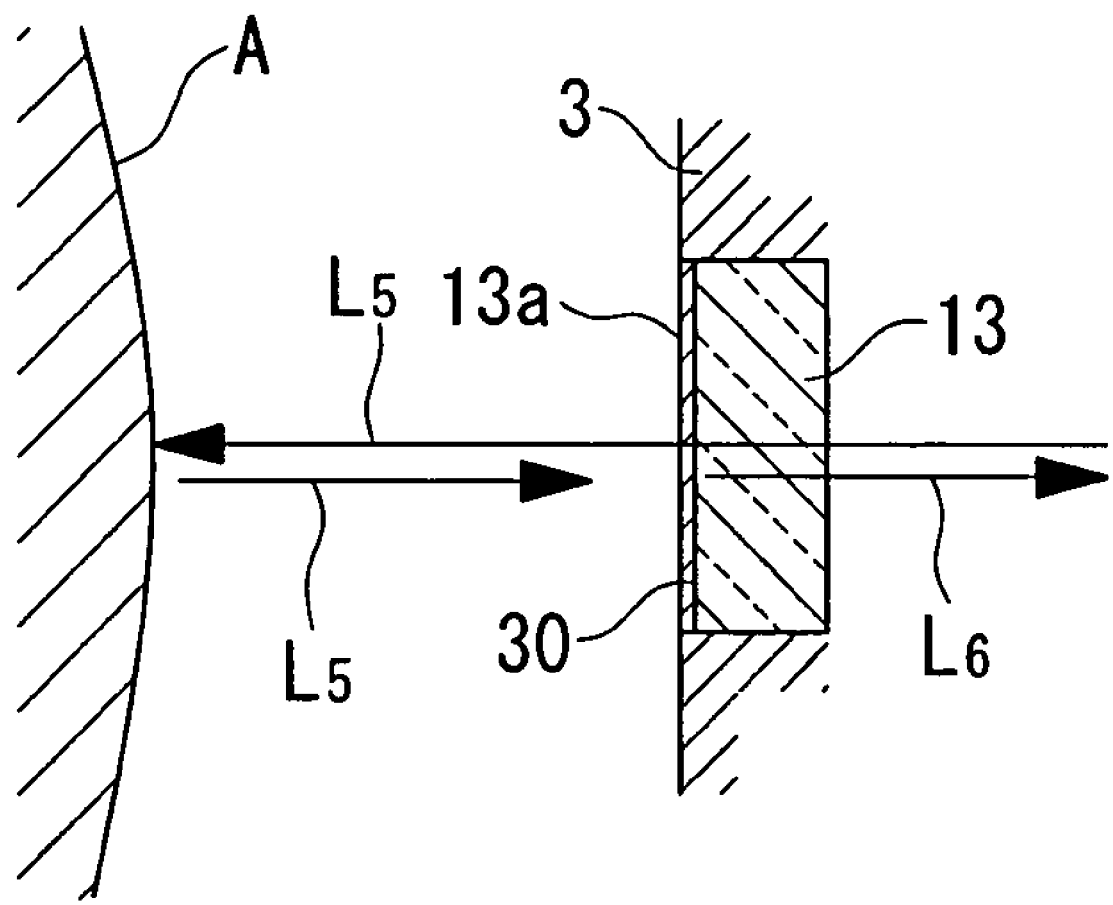
FIG. 4 is a view of a modified example of the cover glass shown in FIG. 2.
Figure 5:
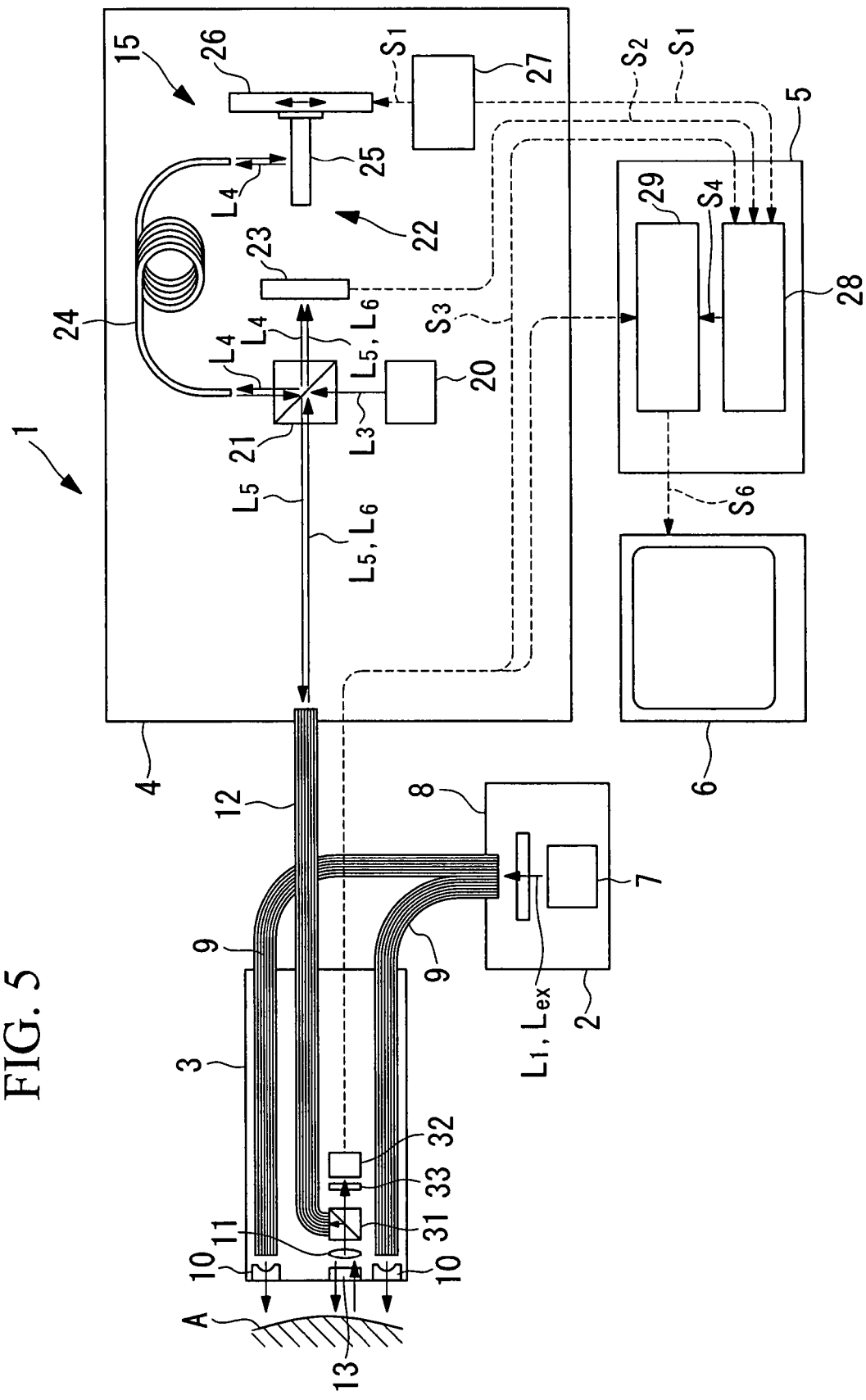
FIG. 5 is a view showing an entire structure of a first modified example of the endoscope observation device shown in FIG. 1.

As the position of the scanning mirror 25 is changed as shown in FIG. 3, the light intensity reaches the peak value at two positions (A1 and A2). The distance between the positions of the scanning mirror 25 corresponding to the peak values is obtained to calculate the distance from the tip surface 13a of the cover glass 13 at the tip of the insertion portion 3 to the surface of the body tissue A accurately.

The image processing unit 5 includes a distance calculation correction unit (correction unit, distance calculation unit) 28 and an image composition unit (image forming unit) 29. The distance calculation correction unit 28 calculates the distance between the positions of the scanning mirror 25 corresponding to the two peak values at each pixel of the interference image pickup element 23 based on the interference image signal $S_2$ output from the interference image pickup element 23 and the position information $S_1$ of the scanning mirror 25 output from the mirror controller 27. The distance calculation correction unit 28 is allowed to accurately measure the distance from the tip surface 13a of the cover glass 13 at the tip of the insertion portion 3 to the respective portions on the surface of the body tissue A, and to correct the brightness information of the fluorescent image based on the calculated distance information.

The brightness information $S_3$ of the fluorescent image detected by the respective pixels of the pickup element 19 of the image detection unit 14 is inversely proportional to the squared distance from the tip surface of the insertion portion 3 to the respective portions on the surface of the body tissue A. Accordingly, the distance calculation correction unit 28 is structured to multiply the correction coefficient that is proportional to the squared measured distance by the brightness information $S_3$ of the respective pixels of the fluorescent image. This makes it possible to obtain the fluorescent image information $S_4$ with the accurate fluorescent quantity on the surface of the body tissue A.

The image composition unit 29 generates composition image information $S_6$ by overlapping the actual image information $S_5$ of the surface of the body tissue A obtained by the pickup element 18 for detecting the white light reflecting on the surface of the body tissue A and the fluorescence image information $S_4$ corrected by the distance calculation correction unit 28 which have been input. The generated information is output to the image display unit 6.

The operation of the above-structured endoscope observation device 1 of the embodiment will be described hereinafter.

In order to perform the observation using the endoscope observation device 1 according to the embodiment, the tip of the insertion portion 3 is inserted into the body cavity such that the white light $L_1$ and the excitation light $L_{ex}$ emitted from the light source unit 2, and the measurement light $L_5$ emitted from the low coherence light source 20 of the detection unit 4 are injected to the insertion portion 3, respectively.

The white light $L_1$ and the excitation light $L_{ex}$ emitted from the light source unit 2 are injected to the light guide 9 of the insertion portion 3 and irradiated to the opposite body tissue A within the body cavity opposite the tip surface of the insertion portion 3 from the tip surface of the light guide 9 arranged at the tip of the insertion portion 3. The white light $L_1$ that reflects on the surface of the body tissue A transmits through the cover glass 13 attached to the insertion portion 3 and is collected by the objective lens 11, which is propagated outside the body cavity by the image guide 12. As the excitation light $L_{ex}$ is irradiated to the body tissue A to excite the fluorescent substance within the body tissue A to generate the fluorescence $L_2$. The generated fluorescence $L_2$ transmits through the cover glass 13 attached to the insertion portion 3 so as to be collected by the objective lens 11 and propagated outside the body cavity by the image guide 12.

When the white light $L_1$ and the fluorescence $L_2$ propagated outside the body cavity by the image guide 12 are injected to the detection unit 4, they are split from the other light by the first dichroic mirror 16 within the detection unit 4. The split white light $L_1$ and the fluorescence $L_2$ are further split by the second dichroic mirror 17 so as to be detected by the pickup elements 18 and 19, respectively. The actual image information $S_5$ of the surface of the body tissue A is obtained based on the detected white light $L_1$, and the brightness information $S_3$ of the fluorescent image which indicates the site at which the fluorescent substance exists within the body tissue A and the degree of the concentration of the fluorescent substance based on the detected fluorescence $L_2$.

The low coherence light $L_3$ emitted from the low coherence light source 20 of the detection unit 4 is split into the reference light $L_4$ and the measurement light $L_5$ by the beam splitter 21. The split measurement light $L_5$ transmits through the first dichroic mirror 16 to be injected to the image guide 12. The measurement light $L_5$ propagated through the image guide 12 transmits from the tip of the image guide 12 to the objective lens 11 and the cover glass 13 so as to be irradiated to the surface of the body tissue A.

The measurement light $L_5$ irradiated to the surface of the body tissue A partially reflects on the surface to transmit through the cover glass 13 and the objective lens 11. It returns to the image guide 12 and propagates therethrough so as to be injected into the detection unit 4. The measurement light $L_5$ transmits through the first dichroic mirror 16 to be split from the white light $L_1$ and the fluorescence $L_2$, and transmits through the beam splitter 21 to be detected by the interference image pickup element 23.

Meanwhile, the reference light $L_4$ split by the beam splitter 21 is injected to the reference light optical path length adjustment unit 22 and propagated by the optical path length determined in accordance with the position of the scanning mirror 25. It then returns to the beam splitter 21. The reference light $L_4$ is reflected by the beam splitter 21 so as to be detected by the interference image pickup element 23 in the state where it is combined with the measurement light $L_5$. The reciprocating optical path length of the reference light $L_4$ from the splitting by the beam splitter 21 of the reference light optical path length adjustment unit 22 to return thereto is set to be substantially the same as that of the measurement light $L_5$. The mirror controller 27 is operated to allow the mirror movement mechanism 26 to move the scanning mirror 25 in one direction. Then at the position where each reciprocating optical path length of the reference light $L_4$ and the measurement light $L_5$ accurately coincides with each other, the light quantity detected by the interference image pickup element 23 reaches the peak value.

In the embodiment, the measurement light $L_5$ reflects not only on the surface of the body tissue A but also on the tip surface 13a of the cover glass 13 to return as the base light $L_6$. As the scanning mirror 25 is moved in one direction, the interference image information $S_2$ output from the interference image pickup element 23 reaches the peak value mainly at two positions as shown in FIG. 3.

The distance calculation correction unit 28 calculates the absolute distance from the tip surface 13a of the cover glass 13 to the body tissue A at each pixel of the interference image pickup element 23 based on the interference image information $S_2$ sent from the interference image pickup element 23 and the position information $S_1$ of the scanning mirror 25 sent from the mirror controller 27. The distance calculation correction unit 28 calculates the correction coefficient proportional to the squared absolute distance for the respective pixels, and multiplies the correction coefficient by the brightness information $S_3$ of the fluorescent image sent from the pickup element 19 for each pixel. Then the fluorescent image information $S_4$ with correct brightness distribution is generated and output to the image composition unit 29.

The image composition unit 29 synthesizes the actual image information $S_5$ on the surface of the body tissue A sent from the pickup element 18 with the fluorescent image information $S_4$ sent from the distance calculation correction unit 28 by overlapping the respective information so as to be output to the image display unit 6. The image display unit 6 displays the actual image on the surface of the body tissue A within the body cavity overlapped with the fluorescent image with the correct brightness distribution. The image composition unit 29 may be structured to output the actual image information $S_5$ and the fluorescent image information $S_4$ independently to the image display unit 6 as necessary. This allows the image display unit 6 to selectively display the actual image within the body cavity, the fluorescent image, and the image both actual image and the fluorescent image overlapped.

In the endoscope observation device 1 of the embodiment, the brightness information $S_3$ of the fluorescent image obtained by the pickup element 19 is corrected using the absolute distance from the tip surface of the insertion portion 3 to the body tissue A. This makes it possible to allow the image display unit 6 to display the fluorescent image with the correct brightness distribution even in such cases as the tip surface of the insertion portion 3 is inclined with respect to the surface of the body tissue A as the object subjected to the image pickup, the surface of the body tissue A as the object subjected to the image pickup curves, or the body tissue A has rough surface. Accordingly, the observer who monitors the image display unit 6 is allowed to identify the site of the fluorescent substance within the body tissue A or to determine the level of the concentration of the fluorescent substance correctly.

The distance measurement is performed using the low coherence light $L_3$ such that the optical system for the distance measurement may be commonly used for obtaining the images, thus making the device compact.

In the embodiment, the base light $L_6$ that returns after reflecting on the tip surface 13a of the cover glass 13 is detected. However, the invention is not limited to the aforementioned structure. A reflective film 30 may be formed on the tip surface 13a of the cover glass 13 so as to positively allow the base light $L_6$ to return after reflecting thereon. This may enhance the intensity of the base light $L_6$ that returns after reflecting on the tip surface 13a of the cover glass 13, thus allowing further accurate detection of the position of the tip surface 13a.

In the embodiment, the base light $L_6$ that returns after reflecting on the tip surface 13a of the cover glass 13 is detected. However, a reflective member (not shown) such as the reflective film may be disposed at the position remote from the tip surface 13a of the cover glass 13 at a known interval to detect the base light $L_6$ that returns after reflecting the reflective member. The detected value may be converted into the distance between the tip surface 13a of the cover glass 13 and the surface of the body tissue A.

In the embodiment, all the white light $L_1$, the fluorescence $L_2$ and the measurement light $L_5$ returning from the body tissue A are propagated to the detection unit 4 via the image guide 12, and then detected therein. However, the measurement light $L_5$ may only be returned to the detection unit 4 so as to be detected therein, and the white light $L_1$ and the fluorescence $L_2$ may be subjected to the image pickup by the pickup element 32 adjacent to the tip of the insertion portion 3 after being split by the dichroic mirror 31 also adjacent to the tip of the insertion portion 3. A reference numeral 33 in the drawing denotes a barrier filter which cuts the excitation light $L_{ex}$.

The actual image information $S_5$ of the white light $L_1$ and the brightness information $S_3$ of the fluorescent image of the fluorescence $L_2$ are output as the electric signals outside the body. The distance calculation correction unit 28 receives inputs of the brightness information $S_3$ of the fluorescent image, and the image composition unit 29 receives the input of the actual image information $S_5$ of the white light $L_1$. A filter turret (not shown) with a plurality of filters may be prepared for the light source unit 2 such that the image information is obtained through the frame sequential method.

Figure 6:
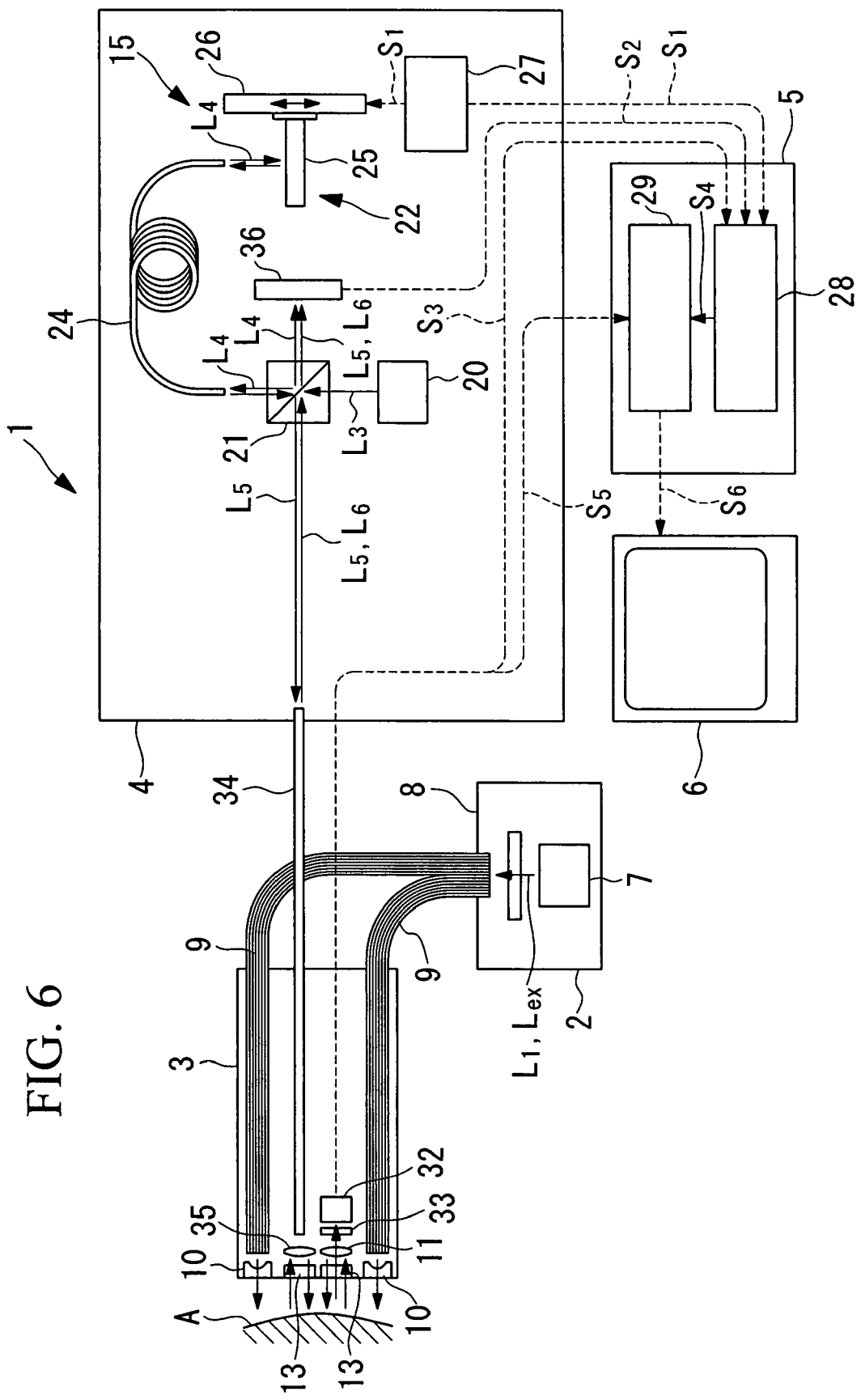
FIG. 6 is a view showing an entire structure of a second modified example of the endoscope observation device shown in FIG. 1.

Referring to FIG. 6, the optical system for the distance measurement may be completely separated from the optical system for obtaining the image such that the measurement light $L_5$ guided from the low coherence light source 20 through the optical fiber (measurement light system) 34 such as the single mode fiber is irradiated to the surface of the body tissue A by an objective lens 35 separated from the object lens 11 for obtaining the image to interfere the measurement light $L_5$ that returns after reflecting on the surface with the reference light $L_4$ for measuring the distance. In this case, the interference image pickup element 36 for detecting the measurement light $L_5$ may be the photo diode as the optical detector, for example. This makes it possible to improve the resolution of the distance measurement.

Figure 7:
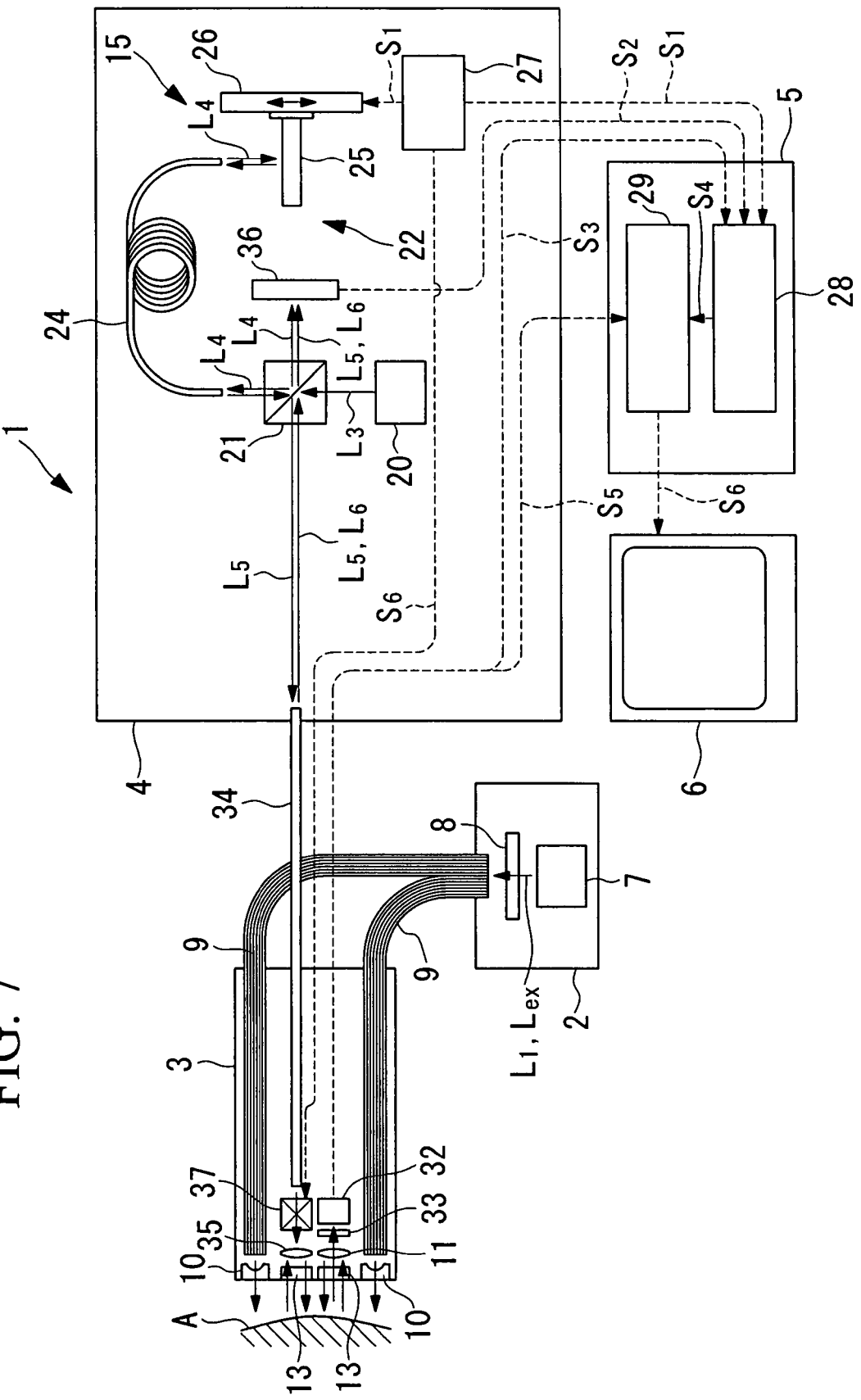
FIG. 7 is a view showing an entire structure of a third modified example of the endoscope observation device shown in FIG. 1.

In the aforementioned case, the arrangement of an optical scanner 37 such as the scan mirror for two-dimensionally scanning the measurement light $L_5$ radiated from the tip of the optical fiber 34 allows the two-dimensional measurement of the distance between the tip surface of the insertion portion 3 and the surface of the body tissue A as shown in FIG. 7. The mirror controller 27 is operated to control the scanning position performed by the optical scanner 37, and the position information $S_6$ relevant thereto is also transmitted to the distance calculation correction unit 28. The distance between the insertion portion 3 and the body tissue A at the corresponding position may be calculated accurately.

Figure 8:
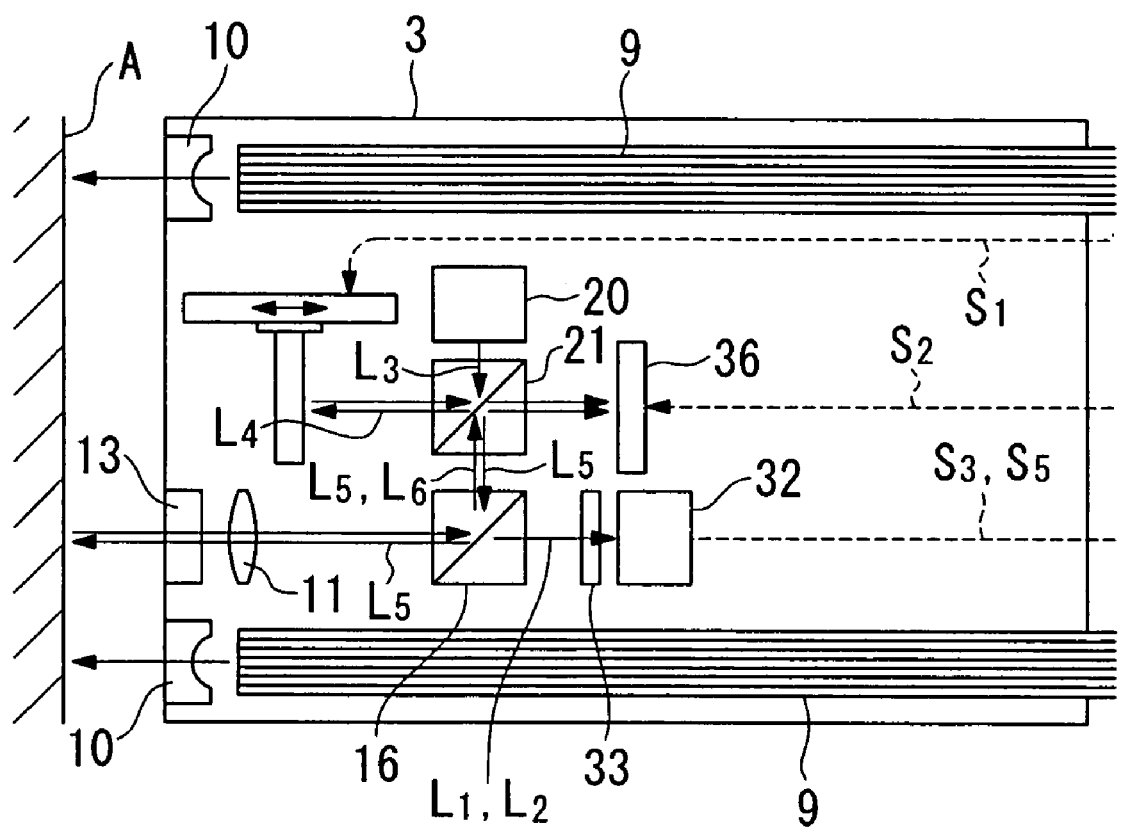
FIG. 8 is a view showing a longitudinal sectional view of an insertion portion as a fourth modified example of the endoscope observation device shown in FIG. 1.

If the tip of the insertion portion 3 is provided with the low coherence light source 20, the beam splitter 21, the interference image pickup element 36, the scanning mirror 25 and the mirror movement unit 26 as shown in FIG. 8, the measurement light $L_5$ does not have to be propagated for an elongated distance. This also makes it possible to obtain all the detected image information $S_2$, $S_3$ and $S_5$ as the electric signals outside the body.

Figure 9:
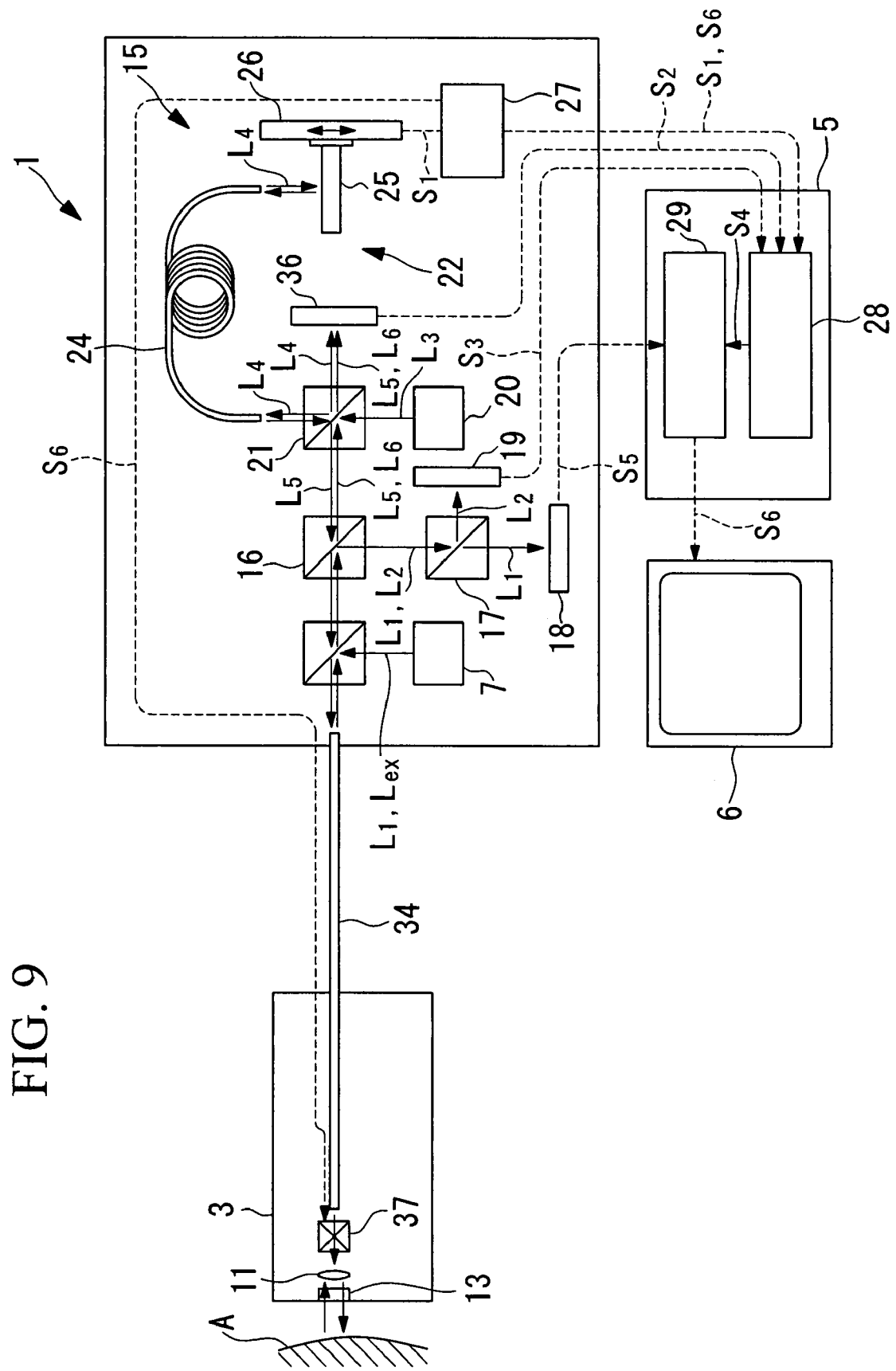
FIG. 9 is a view showing an entire structure of a fifth modified example of the endoscope observation device shown in FIG. 1.

Referring to FIG. 7, only the measurement light $L_5$ is propagated by the optical fiber 34 such as the single mode fiber. However, the white light $L_1$, the excitation light $L_{ex}$ and the measurement light $L_5$ may be guided to the tip of the insertion portion 3 by the optical fiber 34 such as the single mode fiber so as to be two-dimensionally scanned by the optical scanner 37 like the scan mirror attached to the tip of the insertion portion 3 as shown in FIG. 9. This makes it possible to make all the optical systems commonly used, resulting in the compact structure.

Figure 10:
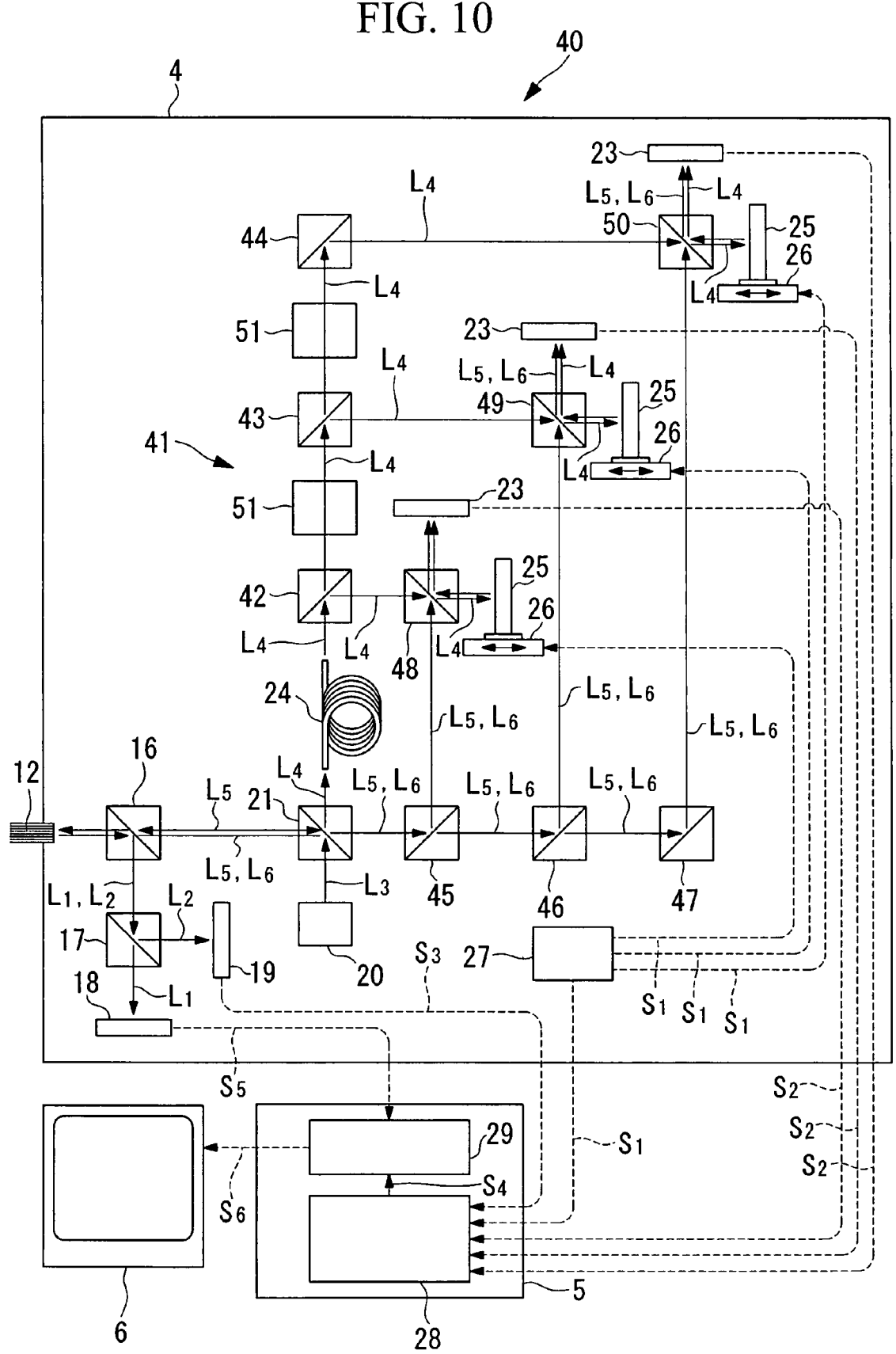
FIG. 10 is a diagram showing a detection unit of the endoscope observation device according to a second embodiment of the invention.

An endoscope observation device 40 according to the second embodiment of the invention will be described referring to FIG. 10.

The same components as those of the endoscope observation device 1 according to the first embodiment as described above will be designated with the same reference numerals and explanations thereof, thus, will be omitted.

The endoscope observation device 40 of the embodiment is different from the endoscope observation device 1 according to the first embodiment in the structure of the reference light optical path length adjustment unit 41.

In the embodiment, the reference light optical path length adjustment unit (optical path length adjustment unit) 41 includes a plurality of beam splitters (reference light split unit) 42, 43 and a mirror 44 for splitting the reference light $L_4$ propagated by the fiber bundle 24 into a plurality of lights, a plurality of scanning mirrors 25 which reflect the respective split reference lights $L_4$, a plurality of mirror movement mechanisms 26 that move those scanning mirrors 25, respectively, a plurality of beam splitters 45, 46 and a mirror 47 for splitting the measurement light $L_5$ and the base light $L_6$ which have transmitted through the beam splitter 21 after returning from the insertion portion 3 into a plurality of lights, a plurality of beam splitters 48 to 50 that combine the plurality pairs of the reference light $L_4$, the measurement light L5 and the base light $L_6$ which have been split by those beam splitters 42, 43, 45 and 46, and a plurality of interference image pickup elements 23 that detect the plurality of pairs of the reference light $L_4$, the measurement light $L_5$ and the base light $L_6$ that have been combined through the beam splitters 48 to 50. A reference numeral 51 in the drawing denotes a glass plate formed of glass at the refractive index in the range from 1.5 to 1.8 for substantially extending the optical path length.

The optical path length on which the measurement light $L_5$ split by the beam splitter 21 is irradiated to the surface of the body tissue A via the image guide 12, returns after reflecting via the image guide 12, transmits through the first dichroic mirror 16 and the beam splitter 21, and reaches the respective beam splitters 45, 46 or the mirror 47 after being reflected by the respective beam splitters 45, 46 or the mirror 47 is set to be different. The optical path length on which the reference light $L_4$ split by the beam splitter 21 transmits through the fiber bundle 24 to be reflected by the beam splitters 42, 43 or the mirror 44, further transmits through the beam splitters 48 to 50 to be turned at the respective scanning mirrors 25 to reach the respective beam splitters 48 to 50 is set to be substantially the same as that of the measurement light $L_5$ that reaches the same beam splitters 48 to 50.

Each range of the optical path length of the reference light $L_4$ adjusted by the respective scanning mirrors 25 is set to be adjacent with each other with no gap. The range of the optical path length of the reference light $L_4$ adjusted by the respective scanning mirror 25 may be adjacent with each other without being overlapped. Alternatively, the range may be overlapped.

The endoscope observation device 40 according to the embodiment is provided with a plurality of interference image pickup elements 23 to allow a plurality of the interference image pickup elements 23 to cover the range of the distance measurement from the tip of the insertion portion 3 to the surface of the body tissue A. Accordingly, the range for the distance measurement may be increased without enlarging the optical path length adjustment range of the reference light $L_4$ by the respective scanning mirrors 25. As a result, the displacement range of the scanning mirror 25 may be reduced to make the time required for measuring the distance short, thus accelerating the image processing.

An endoscope observation device 60 according to the third embodiment of the invention will be described referring to FIG. 11.

The same components as those of the endoscope observation unit 40 according to the second embodiment will be designated with the same reference numerals, and explanations thereof, thus, will be omitted.

Figure 11:
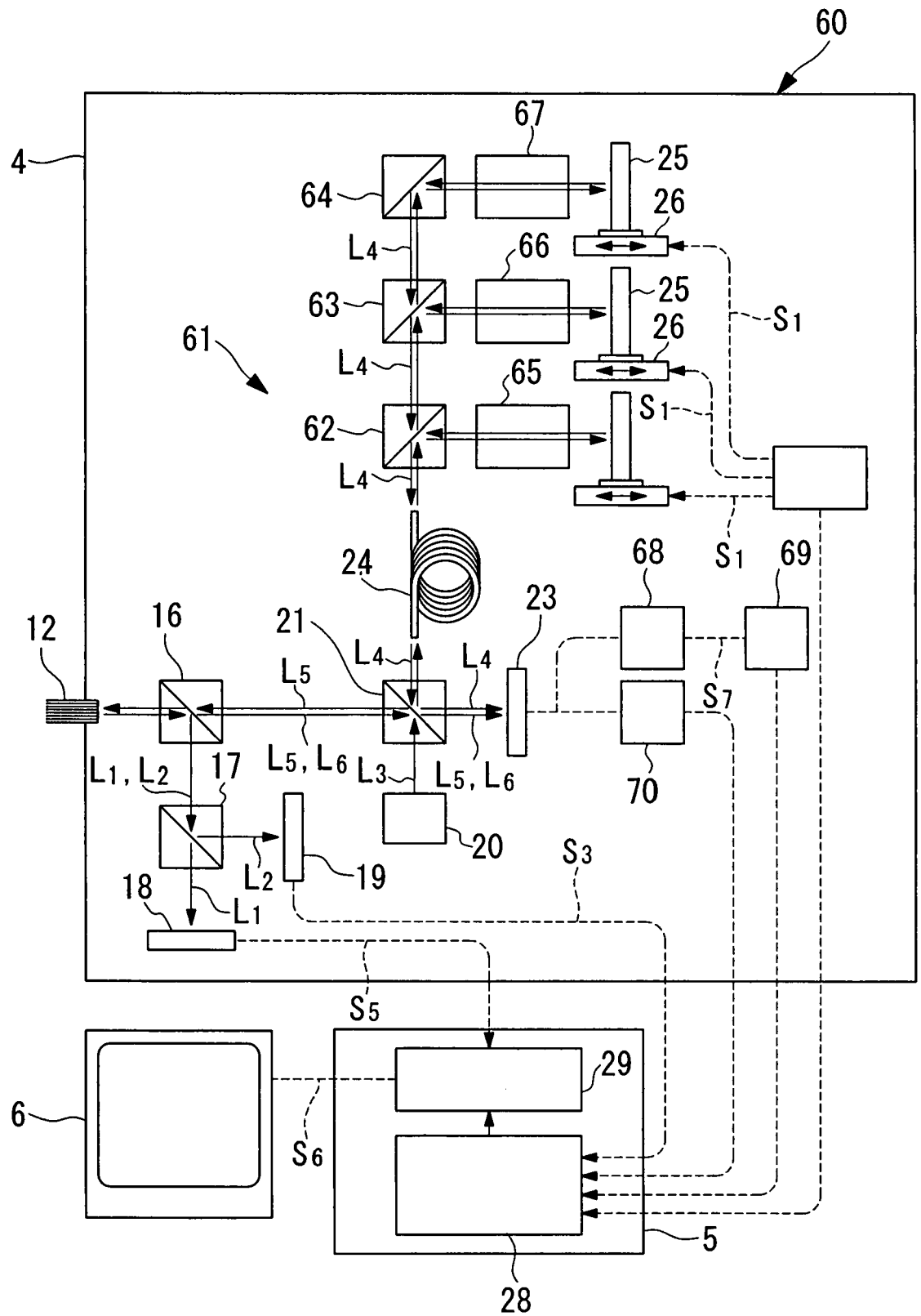
FIG. 11 is a diagram showing a detection unit of the endoscope observation device according to a third embodiment of the invention.

The endoscope observation device 60 of the embodiment is different from the endoscope observation device 40 according to the second embodiment in the structure of the reference light optical path length adjustment unit 61 as shown in FIG. 11.

In the embodiment, the reference light optical path length adjustment unit (optical path length adjustment unit) 61 includes a plurality of beam splitters 62, 63 and a mirror 64 for splitting the reference light $L_4$ propagated by the fiber bundle 24 into a plurality of lights, optical modulators 65 to 67 for modulating the plurality of split reference lights $L_4$ at the different frequencies, a plurality of scanning mirrors 25 which reflect the modulated split reference lights $L_4$, a plurality of mirror movement mechanisms 26 that move those scanning mirrors 25, respectively, a spectrum analyzer (frequency detector) 68 for subjecting the output signal from the interference image pickup element 23 to the frequency analysis, and a reference light identifying unit 69 for identifying the reference light $L_4$ that causes the interference in accordance with the frequency analysis result $S_7$ performed by the spectrum analyzer 68. A reference numeral 70 in the drawing denotes a filter.

Each optical path length on which the reference lights $L_4$ split by the beam splitter 21 transmits through the fiber bundle 24 to be reflected by the beam splitters 62, 63 or the mirror 64, transmits through the respective optical modulators 65 to 67 to be turned by the respective scanning mirrors 25 to reach the beam splitter 21 on the same optical path is set to be different. Each range of the optical path length of the reference lights $L_4$ adjusted by the respective scanning mirrors 25 is set to be adjacent with each other with no gap. The range of the optical path length of the reference light $L_4$ adjusted by the respective scanning mirrors 25 may be adjacent with each other without being overlapped. However, the ranges may be overlapped with each other.

In the above structured endoscope observation device 60 of the embodiment, the reference light $L_4$ split by the beam splitter 21 to transmit through the fiber bundle 24 is reflected by the beam splitters 62, 63 or the mirror 64 so as to be split into a plurality of, for example, three lights. Each split light is frequency modulated by the corresponding optical modulators 65 to 67 at the different frequency. Thereafter, the plurality of the reference lights $L_4$ are reflected by the respective scanning mirrors 25 to return on the same path. In the aforementioned process, the plurality of the reference lights $L_4$ are combined by the beam splitters 62 and 63, and transmit through the fiber bundle 24 to reach the beam splitter 21. The combined reference light $L_4$ is further combined with the measurement light $L_5$ and the base light $L_6$ returning from the insertion portion 3 in the beam splitter 21 so as to be detected by the interference image pickup element 23.

The reference light $L_4$ that reaches the interference image pickup element 23 is synthesized with the reference light $L_4$ reflected by the plurality of scanning mirrors 25 to be propagated through the plurality of optical paths each having the different length. In the embodiment, the reference lights $L_4$ passing through the respective optical paths are modulated to have different frequencies, and subjected to the frequency analysis by the spectrum analyzer 68 after being detected by the interference image pickup element 23. The reference light identifying unit 69 determines as to which frequency of the interference image subjected to the frequency analysis by the spectrum analyzer 68 has a peak value such that the reference light $L_4$ that causes the interference may be easily identified.

Based on the position information $S_1$ of the scanning mirror 25 disposed on the optical path of the reference light $L_4$ identified by the reference light identifying unit 69, the distance between the tip surface of the insertion portion 3 and the surface of the body tissue A may be accurately measured.

Like the endoscope observation device 40 of the second embodiment, in the endoscope observation device 60 of the embodiment, the distance measurement range may be greatly enlarged without increasing the range where each of the scanning mirrors 25 displaces. The structure of the endoscope observation device 60 has the simple structure compared with that of the endoscope observation device 40 of the second embodiment as the single interference image pickup element 23 detects the measurement light $L_5$ and the base light $L_6$ without being split, resulting in the compact structure.

An endoscope observation device 80 according to a fourth embodiment will be described referring to FIG. 12.

The same components as those of the endoscope observation device 1 of the first embodiment will be designated with the same reference numerals, and explanations thereof, thus, will be omitted.

Figure 12:
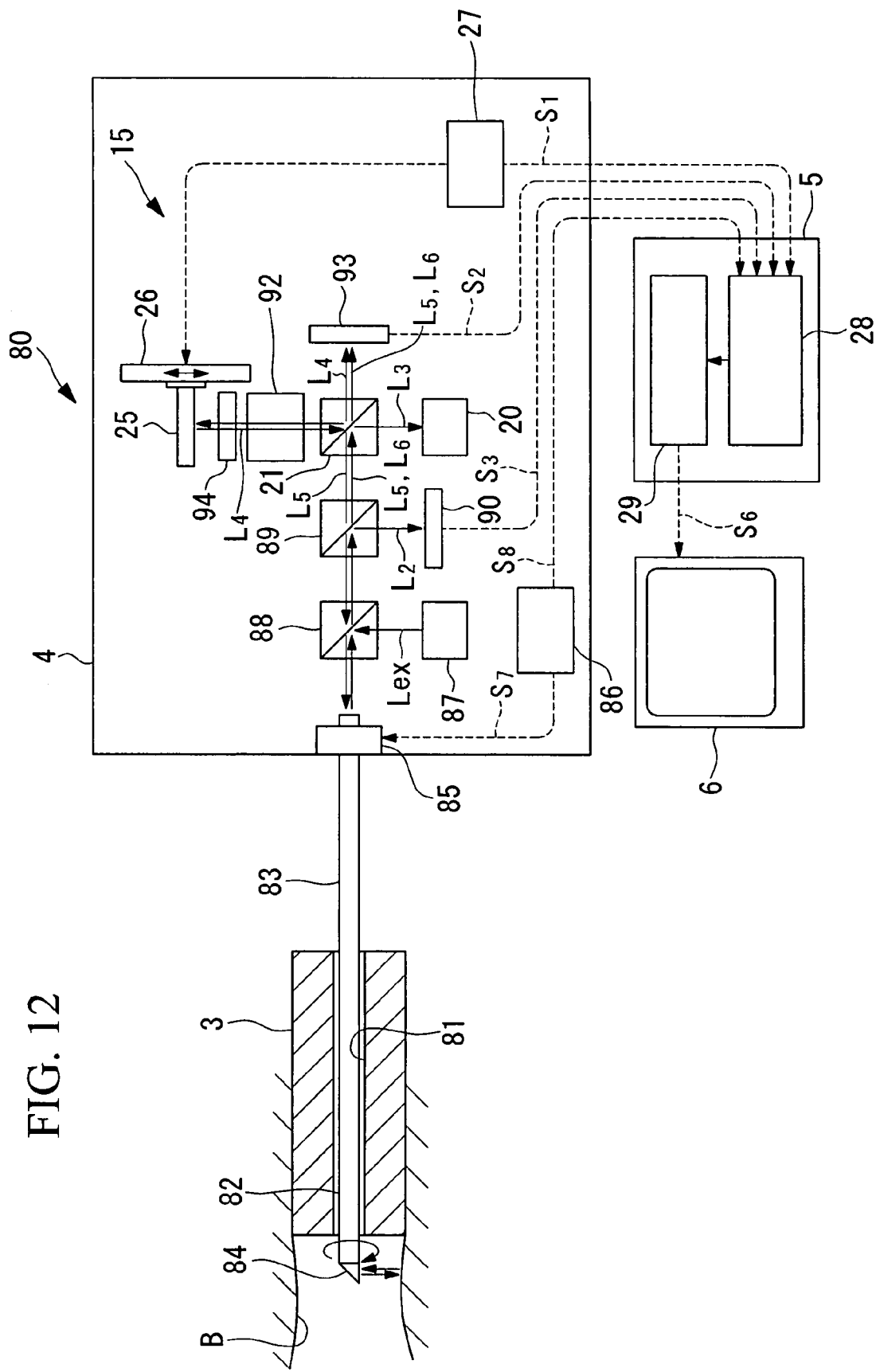
FIG. 12 is a view showing an entire structure of the endoscope observation device according to a fourth embodiment of the invention.

Referring to FIG. 12, the endoscope observation device 80 of the embodiment includes a probe 82 to be inserted into a forceps channel 81 of the long and thin insertion portion 3, and an optical fiber (measurement optical system) 83 connected to the probe 82 and the detection unit 4 such as the single mode fiber.

A mirror (light emitting portion, light receiving portion) 84 that bends the optical axis at 90° is attached to the tip of the probe 82. The probe 82 further includes a rotator 85 that rotates the probe 82 at 360° around its axis and a probe controller 86 that controls the rotator 85.

The detection unit 4 includes an excitation light source 87 that emits the excitation light $L_{ex}$, a first dichroic mirror 88 that injects the excitation light $L_{ex}$ from the excitation light source 87, a second dichroic mirror 89 that splits the fluorescence $L_2$ returning from the probe 82, an optical detector 90 that detects the fluorescence $L_2$ and a distance measurement unit 15.

The optical detector 90 formed of a device for detecting the brightness of the fluorescence $L_2$ such as a photo diode is employed to obtain the strip-shaped image over the entire periphery using the brightness information $S_3$ of the fluorescence $L_2$ obtained at each rotational angular position of the mirror 84 at the tip of the probe 82, and the rotational angular position information $S_8$ of the mirror 84 at that time. The insertion portion 3 that has been inserted into a body cavity B is moved along its axis as a whole or the movement mechanism 91 is operated to move the probe 82 in the axial direction with respect to the insertion portion 3 such that a plurality of the strip-shaped images over the entire periphery are obtained while being shifted in the axial direction. This makes it possible to obtain the fluorescent image over the wide range in the axial direction.

The distance measurement unit 15 which is the same as the one shown in FIG. 1 employs a glass plate 92 for extending the actual optical path length in place of the fiber bundle 24 for keeping the optical path length of the reference light $L_4$, thus realizing the compact structure. A detector 93 of the distance measurement unit 15 is formed of a photo diode, for example. An optical modulator 94 is disposed between the glass plate 92 and the scanning mirror 25.

An acoustic optical modulator (AOM) or an electric optical modulator (EOM) may be employed as the optical modulator 94. The optical modulator 94 changes the frequency of the reference light $L_4$ to be different from those of the measurement light $L_5$ and the base light $L_6$ for the purpose of causing the beat in the light formed by combining the reference light $L_4$, the measurement light $L_5$ and the base light $L_6$. It is preferable to set the beating frequency to be higher than the maximum frequency component of the combined light twice or more. That is, it is preferable to set the value of the change in the frequency of the reference light $L_4$ to be greater than the maximum frequency component of the combined light twice or more. The maximum frequency component of the combined light is proportional to the value obtained by multiplying the scanning frequency of the scanning mirror 25 by the width of the tomogram of the obtained specimen in the depth direction and the inverse number of the resolution value. The optical modulator 94 may be disposed on the optical path of the measurement light $L_5$. A band-pass filter (not shown) for extracting the signal at the beating frequency from the interference brightness information $S_2$ is provided at the side where the interference brightness information $S_2$ is input from the distance calculation correction unit 28 in the image processing unit 5.

In the above-structured endoscope observation device 80 of the embodiment, the excitation light $L_{ex}$ emitted from the excitation light source 87 is reflected by the first dichroic mirror 88 and injected to the optical fiber 83. The excitation light $L_{ex}$ injected to the optical fiber 83 propagates therethrough and is injected to the probe 82. It is bent at 90° by the mirror 84 at the tip of the probe 82 to be radiated in the lateral direction. It is then irradiated to the inner wall surface of the laterally positioned body cavity B.

The fluorescence $L_2$ generated by irradiation of the excitation light $L_{ex}$ returns into the optical fiber 83 via the mirror 84 at the tip of the probe 82. The fluorescence, $L_2$ that has been returned into the optical fiber 83 propagates therethrough and transmits through the first dichroic mirror 88. It is reflected by the second dichroic mirror 89 to be detected by the optical detector 90. The brightness information $S_3$ generated through detection of the fluorescence $L_2$ by the optical detector 90 is transmitted to the distance calculation correction unit 28 together with the rotational angular position information $S_8$ of the probe 82 output from the probe controller 86.

Meanwhile, in the distance measurement unit 15, the light obtained by combining the reference light $L_4$, the measurement light $L_5$ and the base light $L_6$ is detected by the detector 93 to allow the interference brightness information $S_2$ sent from the detector 93 is transmitted to the distance calculation correction unit 28 together with the position information $S_1$ of the scanning mirror 25 such that the distance between the tip surface of the probe 82 and the inner wall surface of the body cavity B is calculated. The light obtained by combining the reference light $L_4$, the measurement light $L_5$ and the base light $L_6$ exhibits the beat owing to the change in the frequency of the reference light $L_4$ modulated by the optical modulator 94. Accordingly, the interference brightness information $S_2$ sent from the detector 93 is input to the image processing unit 5 in the presence of the beat, and transmitted to the distance calculation correction unit 28 after extraction of the component of the beating frequency by the band-pass filter so as to be used for calculating the distance.

In the distance calculation correction unit 28, the fluorescent brightness information $S_3$ sent from the optical detector 90 is corrected based on the calculated distance, which will be accumulated in the image composition unit 29. The brightness information $S_3$ of the fluorescence $L_2$ obtained at each rotational angular position during the rotation of the probe 82 at 360° is accumulated in the image composition unit 29 after the correction based on the distance calculated at each time. This makes it possible to generate the strip-shaped fluorescent image information with the correct brightness over the entire periphery.

Figure 13:
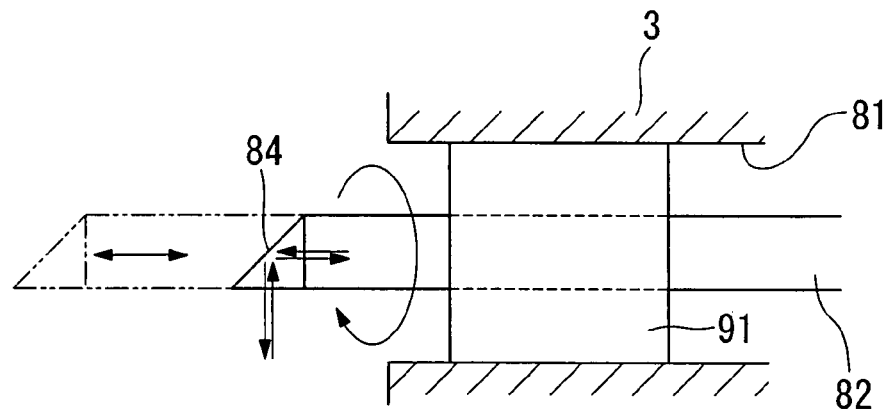
FIG. 13 is a view showing a tip as a first modified example of the endoscope observation device shown in FIG. 12.

Assuming that the probe 82 is moved in the axial direction by the movement mechanism 91 shown in FIG. 13, the fluorescent image in a predetermined range along the axis may be obtained.

As the band-pass filter extracts the component of the beating frequency generated by the optical modulator 94 from the interference brightness information $S_2$, the component of the signal relevant to the interference of the reference light $L_4$, the measurement light $L_5$ and the base light $L_6$ may be extracted from the interference brightness information $S_2$ such that the other noise component may be eliminated.

Figure 14:
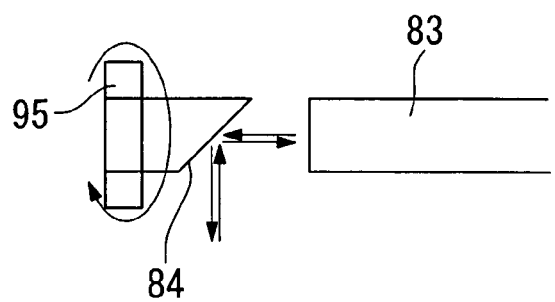
FIG. 14 is a view showing a tip as a second modified example of the endoscope observation device shown in FIG. 12.

In the embodiment, the probe 82 having the mirror 84 attached to its tip is rotated around its axis. It may be structured to have the optical fiber 83 fixed as shown in FIG. 14 such that the mirror 84 obliquely arranged opposite the end surface of the end surface of the optical fiber 83 is rotated around its axis by the actuator such as a hollow motor 95, for example.

Figure 15:
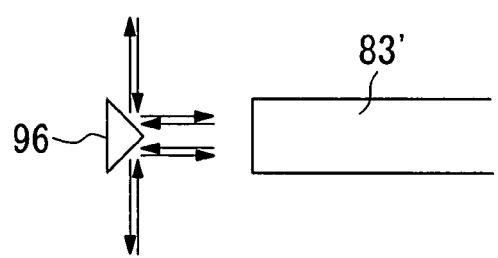
FIG. 15 is a view showing a tip as a third modified example of the endoscope observation device shown in FIG. 12.

A conical mirror 96 as shown in FIG. 15 may be attached to the opposite tip of a fiber bundle 83' so as to obtain the fluorescent image over the entire periphery at a time.

The invention may be applied to the observation device equipped with no insertion portion 3 (not shown).

An endoscope observation device 100 according to a fifth embodiment of the invention will be described referring to FIGS. 16 and 17.

The same components as those of the aforementioned endoscope observation device 80 of the fourth embodiment will be designated with the same reference numerals and explanations thereof, thus will be omitted.

Figure 16:
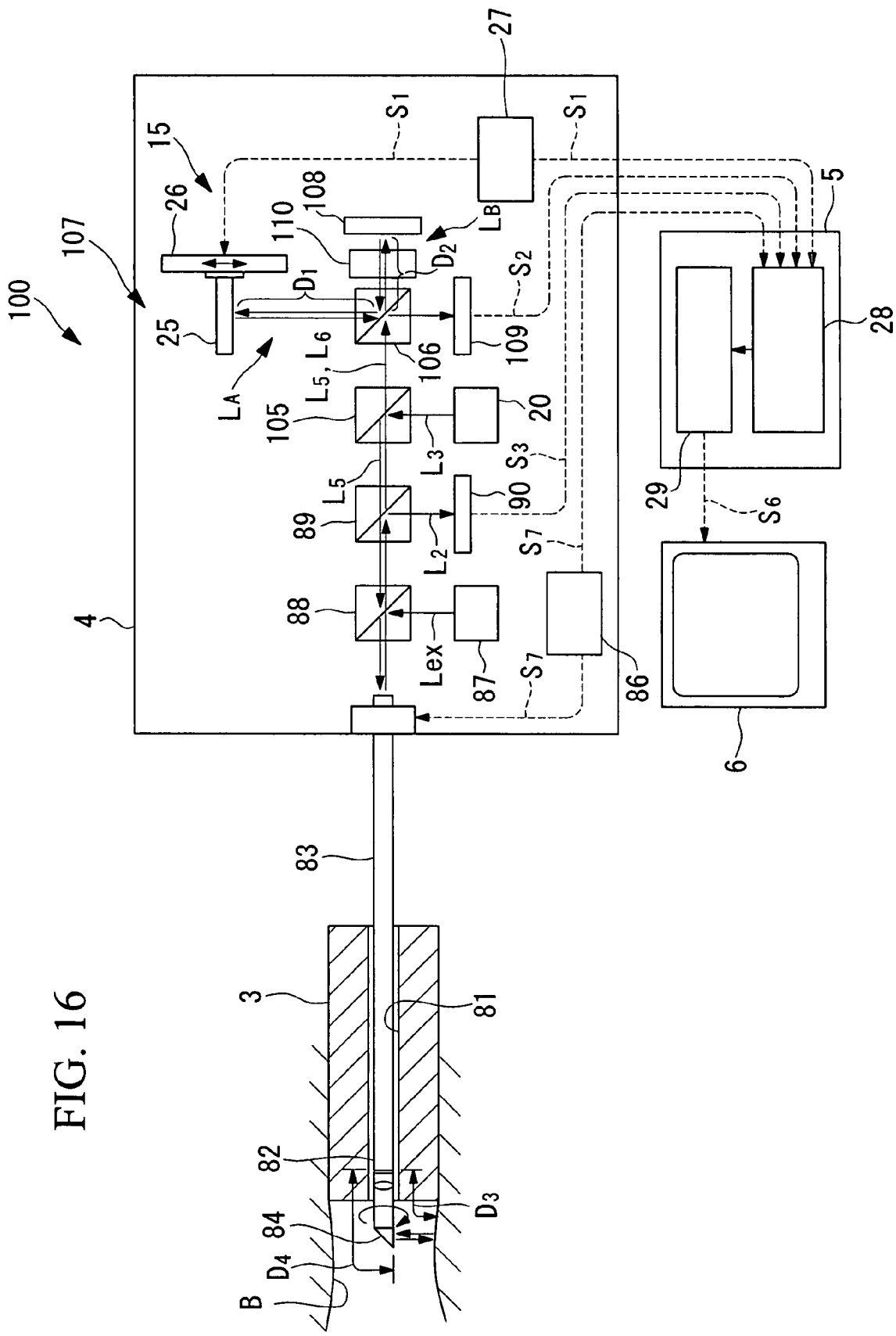
FIG. 16 is a view showing an entire structure of the endoscope observation device according to a fifth embodiment of the invention.
Figure 17:
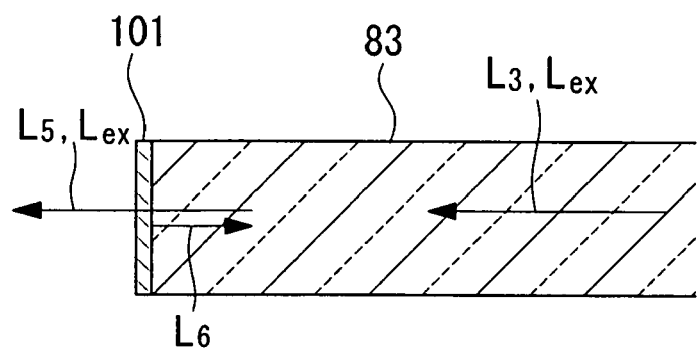
FIG. 17 is a longitudinal sectional view showing a semi-transmissive film attached to the tip surface of the optical fiber in the endoscope observation device shown in FIG. 16.

Referring to FIG. 16, the endoscope observation device 100 of the embodiment includes a probe 82 to be inserted into a forceps channel 81 of the long and thin insertion portion 3, an optical fiber 83 that propagates the light from the detection unit 4 to the probe 82, and a semi-transmissive film (base light split unit) 101 attached to the tip of the optical fiber 83 at the intermediate position of the probe 82 in the longitudinal direction.

Figure 18:
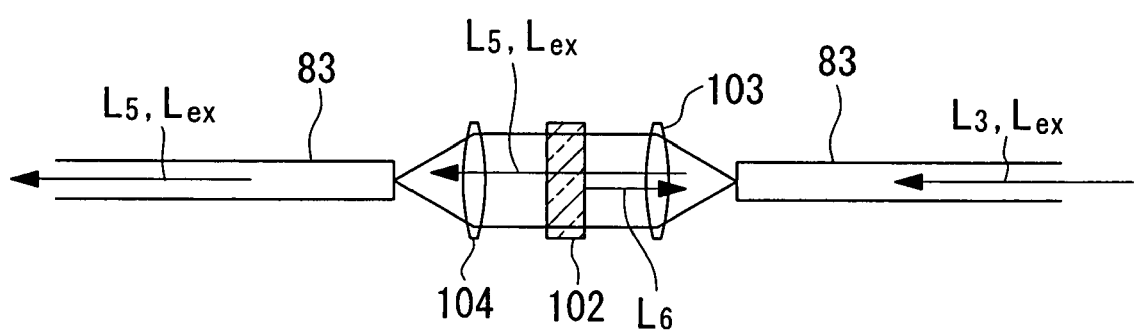
FIG. 18 is a diagram showing a modified example of the semi-transmissive film shown in FIG. 17.

The semi-transmissive film 101 splits part of the low coherence light $L_3$ emitted from the low coherence light source 20 and guided by the optical fiber 83 as the base light $L_6$, and the measurement light $L_5$ as the rest of the low coherence light $L_3$, which are allowed to transmit so as to be guided to the body cavity B as the specimen. In the embodiment shown in FIGS. 16 and 17, the semi-transmissive film 101 is attached to the tip surface of the optical fiber 83. In the case where the measurement optical system includes the relay lens system as shown in FIG. 18, a half mirror 102 may be provided on the optical path of the measurement optical system as the reference light split unit. In the drawings, a reference numeral 103 denotes a collimated lens, and a reference numeral 104 denotes a coupling lens.

The distance measurement unit 15 includes a low coherence light source 20, a first beam splitter 105 that reflects the low coherence light $L_3$ emitted from the low coherence light source 20 to guide the light to the optical fiber 83 while transmitting the measurement light $L_5$ and the base light $L_6$ returning from the optical fiber 83, a second beam splitter (interference light split unit: optical coupler) 106 that splits the measurement light $L_5$ and the base light $L_6$ which have been transmitted through the first beam splitter 105 into two interference optical paths, that is, the first and the second interference optical paths $L_A$ and $L_B$, an optical path length difference adjustment unit 107 that is disposed on the first interference optical path $L_A$ for adjusting the difference in the optical path length between those two interference optical paths $L_A$ and $L_B$, a mirror 108 that is disposed on the second interference optical path $L_B$ for returning the measurement light $L_5$ and the base light $L_6$ through reflection, and a detector 109 that detects the measurement light $L_5$ and the base light $L_6$ which have returned to the second beam splitter 106 to be combined together.

The optical path length difference adjustment unit 107 includes the scanning mirror 25 that returns the measurement light $L_5$ and the base light $L_6$ split to the first interference optical path $L_A$ by the second bema splitter 106 thereto, the mirror movement mechanism (mirror movement unit) 26 that moves the scanning mirror 25 along the first interference optical path $L_A$, and the mirror controller 27 that controls the mirror movement mechanism 26 and outputs the position information $S_1$ of the scanning mirror 25.

The scanning mirror 25 is structured to reciprocally move between the position where the optical path length $D_1$ with respect to the second beam splitter 106 becomes equal to the optical path length $D_2$ from the second beam splitter 106 to the mirror 108 and the position where the optical path length $D_1$ becomes longer than the optical path length $D_2$ by the length $D_3$ from the semi-transmissive film 101 to the inner surface of the body cavity B via the mirror 84. This makes it possible to measure the optical path length $D_3$ between the semi-transmissive film 101 and the inner surface of the body cavity B as the difference between the optical path length $D_1$ of the first interference optical path $L_A$ and the second optical path length $D_2$ of the second interference optical path $L_B$.

The mirror movement mechanism 26 is operated to perform the positional adjustment of the scanning mirror 25 such that the base light $L_6$ returned to the second beam splitter 106 through the first interference optical path $L_A$ interferes with the measurement light $L_5$ returned to the second beam splitter 106 through the second interference optical path $L_B$ when the difference between the optical path length $D_1$ of the first interference optical path $L_A$ and the optical path length $D_2$ of the second interference optical path $L_B$ coincides with the optical path length $D_3$ from the semi-transmissive film 101 to the inner surface of the body cavity B via the mirror 84. When those two optical path lengths $D_1$ and $D_2$ of the respective interference optical paths $L_A$ and $L_B$ coincide with each other accurately, the base lights $L_6$ each passing through the respective interference optical paths $L_A$ and $L_B$ are expected to cause the interference. When the interference occurs, the light intensity detected by the detector 109 reaches the peak value.

The second interference optical path $L_B$ between the second beam splitter 106 and the mirror 108 includes an optical modulator 110 for modulating each frequency of the measurement light $L_5$ and the base light $L_6$ passing through the second interference optical path $L_B$.

The optical modulator 110 changes the frequency of the light passing through the second interference optical path $L_B$ so as to be different from that of the light passing through the first interference optical path $L_A$ in order to cause the beat in the light obtained by combining the base light $L_6$ passing through the first interference optical path $L_A$ and the measurement light $L_5$ passing through the second interference optical path $L_B$, and the light obtained by combining the base lights $L_6$ each passing through those two interference optical paths $L_A$ and $L_B$. The optical modulator 110 may be disposed at the intermediate position of the first interference optical path $L_A$. The image processing unit 5 is provided with the band-pass filter (not shown) for extracting the signal of the beating frequency from the interference brightness information $S_2$ at the side where the interference brightness information $S_2$ is input from the distance calculation correction unit 28.

The distance calculation correction unit 28 is provided with a memory (not shown) that preliminarily stores the optical path length $D_2$ of the second interference optical path $L_B$ and an optical path length $D_4$ from the semi-transmissive film 101 to the tip surface of the probe 82. The distance calculation correction unit 28 calculates the difference between the optical path length $D_1$ of the first interference optical path $L_A$ and the optical path length $D_2$ of the second interference optical path $L_B$ at a time point when the interference occurs between the base light $L_6$ passing through the first interference optical path $L_A$ and the measurement light $L_5$ passing through the second interference optical path $L_B$ in the second beam splitter 106. The absolute distance between the tip surface of the probe 82 and the body cavity B may be calculated based on the value obtained by subtracting the optical path length $D_4$ stored in the memory from the calculated difference.

Specifically, the distance calculation correction unit 28 is structured to calculate the optical path length $D_1$ of the first interference optical path $L_A$ based on the position information $S_1$ of the scanning mirror 25 output from the mirror controller 27. Then the optical path length $D_2$ of the second interference optical path $L_B$ and the optical path length $D_4$ from the semi-transmissive film 101 to the tip surface of the probe 82 are read from the memory, and the sum of the optical path lengths of $D_2$ and $D_4$ is subtracted from the calculated optical path length $D_1$. The distance calculation correction unit 28 is capable of calculating the absolute distance from the tip surface of the probe 82 and the body cavity B.

The operation of the above-structured endoscope observation device 100 of the embodiment will be described.

In the endoscope observation device 100, the excitation light $L_{ex}$ emitted from the excitation light source 87 is reflected by the first dichroic mirror 88 to be injected into the optical fiber 83. The excitation light $L_{ex}$ injected into the optical fiber 83 propagates therethrough to be injected to the probe 82. It is bent at 90° by the mirror 84 attached to the tip of the probe 82 and laterally radiated to the inner wall surface of the body cavity B arranged in the lateral direction.

The fluorescence $L_2$ generated through irradiation of the excitation light $L_{ex}$ returns into the optical fiber 83 via the mirror 84 at the tip of the probe 82. The fluorescence $L_2$ returned into the optical fiber 83 propagates therethrough and transmits the first dichroic mirror 88. It is reflected by the second dichroic mirror 89 to be detected by the optical detector 90. The brightness information $S_3$ generated through detection of the fluorescence $L_2$ by the optical detector 90 is transmitted to the distance calculation correction unit 28 together with the rotational angular position information $S_8$ of the probe 82 output from a probe controller 86.

The low coherence light $L_3$ emitted from the low coherence light source 20 of the detection unit 4 is reflected by the first beam splitter 105 and further injected into the probe 82. The low coherence light $L_3$ propagated through the probe 82 is partially reflected by the semi-transmissive film 101 to be formed as the base light $L_6$, and the rest of the low coherence light is formed as the measurement light $L_5$ that transmits through the semi-transmissive film 101 to be irradiated to the inner surface of the body cavity B.

The base light $L_6$ reflected on the semi-transmissive film 101 and the measurement light $L_5$ returned after reflecting on the inner surface of the body cavity B transmit through the first beam splitter 105, and are split into two interference optical paths, that is, the first and the second optical paths $L_A$ and $L_B$ by the second beam splitter 106. The measurement light $L_5$ and the base light $L_6$ guided through the first interference optical path $L_A$ are reflected by the scanning mirror 25 of the optical path length difference adjustment unit 107, and return to the second beam splitter 106 again. Meanwhile, the measurement light $L_5$ and the base light $L_6$ guided through the second interference optical path $L_B$ have the respective frequencies changed through passage of the optical modulator 110. They are reflected by the mirror 108 to return to the second beam splitter 106 again.

When the position of the scanning mirror 25 is controlled such that the optical path length $D_1$ of the first interference optical path $L_A$ accurately coincides with the sum of the optical path length $D_2$ of the second interference optical path LB and the optical path length $D_3$ from the semi-transmissive film 101 to the inner surface of the body cavity B, the optical path length of the measurement light L5 which is reflected on the inner surface of the body cavity B and injected into the second beam splitter 106 through the second interference optical path $L_B$ coincides with the optical path length of the base light $L_6$ which is split through the semi-transmissive film 101 and injected to the second beam splitter 106 through the first interference optical path $L_A$.

When the optical path length $D_1$ accurately coincides with the optical path length $D_2$, the optical path length of the base light $L_6$ injected into the second beam splitter 106 through the second interference optical path $L_B$ coincides with the optical path length of the base light $L_6$ injected into the second beam splitter 106 through the first interference optical path $L_A$.

The positional adjustment of the scanning mirror 25 is performed such that the measurement light $L_5$ and the base light $L_6$ each passing through the second interference optical path $L_B$ are interfered with the base light $L_6$ passing through the first interference optical path $L_A$ in the second beam splitter 106. At the aforementioned time, the light intensity signal $S_2$ detected by the detector 109 reaches the peak value. Accordingly, the light intensity signal $S_2$ reaches the peak value twice as the position of the scanning mirror 25 is changed.

The distance calculation correction unit 28 calculates the distance between two positions of the scanning mirrors 25 corresponding to the two peak values based on the position information $S_1$ of the scanning mirror 25 such that the optical path length $D_3$ from the semi-transmissive film 101 to the inner surface of the probe 82 is calculated. Then the distance calculation correction unit 28 reads the optical path length $D_4$ from the semi-transmissive film 101 to the tip surface of the probe 82 from the memory, and subtracts the optical path length $D_4$ from the calculated optical path length $D_3$. The distance calculation correction unit 28 is capable of calculating the absolute distance between the tip surface of the probe and the inner surface of the body cavity B.

When the absolute distance between the tip surface of the probe 82 and the inner surface of the body cavity B is calculated, the distance calculation correction unit 28 corrects the brightness information $S_3$ of the fluorescence $L_2$ detected by the optical detector 90 based on the calculated absolute distance. The corrected information is accumulated in the image generation unit 29. The brightness information $S_3$ of the fluorescence $L_2$ obtained at the respective rotational angular positions while rotating the probe at 360° is corrected based on the calculated distance, and accumulated in the image forming unit 29. This makes it possible to generate the strip-shaped fluorescent image information with the correct brightness over the entire periphery.

The band-pass filter serves to extract the component of the beating frequency generated by the optical modulator 94 from the interference brightness information $S_2$. The component of the signal relevant to the interference of the measurement light $L_5$ and the base light $L_6$ each passing through the second interference optical path $L_B$ with the base light $L_6$ passing through the first interference optical path $L_A$ is only extracted from the interference brightness information $S_2$ so as to eliminate the other component of noise.

In the embodiment, the absolute distance between the tip surface of the probe 82 and the inner surface of the body cavity B is obtained based on the distance between two positions of the scanning mirrors 25 corresponding to the two peak values generated in the optical intensity signal $S_2$ detected by the detector 109. However, the following process may be employed for calculating the absolute distance.

In the distance measurement unit 15, when the optical path length $D_1$ from the scanning mirror 25 to the second beam splitter 106 accurately coincides with the sum of the optical path length $D_2$ from the second beam splitter 106 to the mirror 108 and the optical path length $D_3$ from the semi-transmissive film 101 to the inner surface of the body cavity B, the optical path length of the measurement light $L_5$ injected into the second beam splitter 106 through the second interference optical path $L_B$ coincides with the optical path length of the base light $L_6$ injected into the second beam splitter 106 through the first interference optical path $L_A$. The calculation may be performed by replacing the optical path length $D_3$ between the semi-transmissive film 101 and the body cavity B with the difference between the optical path lengths $D_1$ and $D_2$.

If the optical path lengths $D_2$ and $D_4$ are known, the optical path length $D_1$ from the scanning mirror 25 to the second beam splitter 106 may only be obtained for calculating the absolute distance between the tip surface of the probe 82 and the inner surface of the body cavity B. In this case, the scanning mirror 25 is arranged only at the position at which the optical path length $D_1$ accurately coincides with the sum of the optical path lengths $D_2$ and $D_3$. The information of the optical path lengths $D_2$ and $D_4$ is stored in the memory (not shown) of the distance calculation correction unit 28.

In the aforementioned structure, the scanning mirror 25 is subjected to the positional adjustment such that the measurement light $L_5$ passing through the second interference optical path $L_B$ is interfered with the base light $L_6$ passing through the first interference optical path $L_A$ in the second beam splitter 106. At this time, the optical intensity signal detected by the detector 109 reaches the peak value. The optical intensity signal $S_2$ detected by the detector 109 is transmitted to the distance calculation correction unit 28 together with the position information $S_1$ of the scanning mirror 25.

The distance calculation correction unit 28 calculates the difference between the lengths of two interference optical paths $L_A$ and $L_B$ at a time point when the base light $L_6$ passing through the first interference optical path $L_A$ is interfered with the measurement light $L_5$ passing through the second interference optical path $L_B$ in the second beam splitter 106.

Specifically, the distance calculation correction unit 28 calculates the optical path length $D_1$ of the first interference optical path $L_A$ based on the position information $S_1$ of the scanning mirror 25 at a time point when the measurement light $L_5$ passing through the second interference optical path $L_B$ is interfered with the base light $L_6$ passing through the first interference optical path $L_A$. The distance calculation correction unit 28 reads the optical path length $D_2$ of the second interference optical path $L_B$ and the optical path length $D_4$ from the semi-transmissive film 101 to the tip surface of the probe 82 from the memory, and subtracts the sum of the optical path lengths $D_2$ and $D_4$ from the calculated optical path length $D_1$. The distance calculation correction unit 28 is capable of calculating the absolute distance between the tip surface of the probe 82 and the inner surface of the body cavity B.

The position information $S_1$ of the single scanning mirror 25 is only detected to allow calculation of the absolute distance between the tip surface of the probe 82 and the inner surface of the body cavity B, thus reducing the operation range of the scanning mirror 25. Accordingly, the absolute distance may further be easily calculated.

In the embodiment, the semi-transmissive film 101 is attached to the tip surface of the optical fiber 83 disposed at the intermediate position of the probe 82 in the longitudinal direction. Alternatively, it may be arranged at the tip surface of the probe 82.

This makes it possible to coincide the difference between the optical path lengths $D_1$ and $D_2$ of those two interference optical paths $L_A$ and $L_B$ with the absolute distance from the tip surface of the probe 82 to the inner surface of the body cavity B. Storage only of the optical path length $D_2$ of the second interference optical path $L_B$ in the memory of the distance calculation correction unit 28 allows calculation of the absolute distance. This makes it possible to simplify the calculation process with no need of storing the optical path length $D_4$ in the memory.

In the embodiment, the optical path length difference adjustment unit 107 is disposed on the first interference optical path $L_A$. Alternatively, it may be disposed on the second interference optical path $L_B$.

In the endoscope observation device 100 of the embodiment as shown in FIG. 16, the semi-transmissive film 101 may be used for splitting the reference light $L_4$ and the absolute distance from the tip surface of the probe 82 to the inner surface of the body cavity B is calculated using the base light $L_6$ that returns after reflecting on the tip surface (for example, the tip surface of the cover glass) of the probe 82.

The reference light $L_4$, the measurement light $L_5$ and the base light $L_6$ return to the two interference optical paths $L_A$ and LB, respectively. The difference in the optical path length $D_1$ of the first interference optical path $L_A$ between the interference of the reference light $L_4$ with the measurement light $L_5$ and the interference of the reference light $L_4$ with the base light $L_6$ is calculated to accurately obtain the absolute distance between the tip surface of the probe 82 and the inner surface of the body cavity B.

In this case, the optical path length $D_2$ of the second interference optical path $L_B$ and the position information of the semi-transmissive film 101 for splitting the reference light $L_4$ do not have to be stored. The required accuracy for installing the semi-transmissive film 101 or the mirror 108 is not so strict. This makes it possible to easily produce the device as well as simplify arithmetic processing.

In the case where the intensity of the measurement light $L_5$ that returns from the inner surface of the body cavity B or the base light $L_6$ that returns from the tip surface of the probe 82 is relatively low, the interference light with high intensity may be obtained by enhancing the intensity of the reference light $L_4$ interfered with the measurement light $L_5$ and the base light $L_6$. This makes it possible to improve the accuracy of the arithmetic operation of the absolute distance.

Compared with the case where the relatively long optical path for the reference light $L_4$ is required within the detection unit 4 as shown in FIG. 1, the aforementioned structure allows the optical path of the reference light $L_4$ to be disposed within the probe 82, thus reducing the size of the detection unit 4 and further making the endoscope observation device 100 compact.

What is claimed is:

1. An endoscope observation device in which a tip of an insertion portion to be inserted into a body cavity is provided with a light emitting portion that irradiates light rays to a specimen and a light receiving portion that receives an observation light returning from the specimen for forming an image of the observation light received by the light receiving portion, comprising:
    a distance measurement unit that calculates an absolute distance between the tip of the insertion portion and the specimen through an interference of a low coherence light;
    a correction unit that corrects a piece of brightness information of the observation light based on the absolute distance calculated by the distance measurement unit;
    an image forming unit that forms an image of the specimen based on the brightness information of the observation light corrected by the correction unit; and
    an optical element that splits the low coherence light from the observation light.

2. The endoscope observation device according to claim 1, wherein the insertion portion includes an optical system that guides the observation light and the low coherence light coaxially.

3. An endoscope observation device in which a tip of an insertion portion to be inserted into a body cavity is provided with a light emitting portion that irradiates light rays to a specimen and a light receiving portion that receives an observation light returning from the specimen for forming an image of the observation light received by the light receiving portion, comprising:
    a distance measurement unit that calculates an absolute distance between the tip of the insertion portion and the specimen through an interference of a low coherence light;
    a correction unit that corrects a piece of brightness information of the observation light based on the absolute distance calculated by the distance measurement unit; and
    an image forming unit that forms an image of the specimen based on the brightness information of the observation light corrected by the correction unit;
    wherein the insertion portion includes a base light split unit that is fixed in the insertion portion for splitting the low coherence light into a base light and a measurement light and for guiding the measurement light to the specimen; and the distance measurement unit includes a distance calculation unit that calculates the absolute distance between the tip of the insertion portion and the specimen based on a difference between an optical path length from the base light split unit and the specimen measured using at least the base light and the measurement light returning from the specimen as an interference light and an optical path length from the base light split unit and the tip of the insertion portion.

4. The endoscope observation device according to claim 3, wherein:
the distance calculation unit includes
a low coherence light source;
a reference light split unit that splits the reference light from the low coherence light emitted from the low coherence light source, and guides a rest of the low coherence light to the insertion portion;
an optical path length adjustment unit that adjusts an optical path length of the reference light split by the reference light split unit; and
an optical coupler that combines the measurement light and the base light returning from the specimen with the reference light returning from the optical path length adjustment unit to cause an interference; and
the distance calculation unit calculates the absolute distance between the tip of the insertion portion and the specimen based on a value obtained by subtracting the optical path length from the base light split unit to the tip of the insertion portion from a difference between a first optical path length of the reference light at a time point when the interference of the measurement light with the reference light occurs in the optical coupler and a second optical path length of the reference light at a time point when the interference of the base light with the reference light occurs in the optical coupler.

5. The endoscope observation device according to claim 3, wherein:
the distance measurement unit includes:
a low coherence light source;
an interference light split unit that splits the measurement light and the base light returning from the specimen into two interference optical paths;
an optical path length difference adjustment unit that adjusts an optical path length difference between the two interference optical paths; and
an optical coupler that combines the low coherence lights each passing through the two interference light paths to cause the interference; and
the distance calculation unit calculates the absolute distance between the tip of the insertion portion and the specimen based on a value obtained by subtracting an optical path length from the base light split unit to the tip of the insertion portion from the optical path length difference between the two interference optical paths at a time point when an interference between the measurement light and the base light occurs in the optical coupler.

6. An endoscope observation device in which a tip of an insertion portion to be inserted into a body cavity is provided with a light emitting portion that irradiates light rays to a specimen and a light receiving portion that receives an observation light returning from the specimen for forming an image of the observation light received by the light receiving portion, comprising:

a distance measurement unit that calculates an absolute distance between the tip of the insertion portion and the specimen through an interference of a low coherence light;
a correction unit that corrects a piece of brightness information of the observation light based on the absolute distance calculated by the distance measurement unit; and
an image forming unit that forms an image of the specimen based on the brightness information of the observation light corrected by the correction unit;
wherein the insertion portion includes a base light split unit fixed to a tip of the insertion portion for splitting the low coherence light into a base light and a measurement light for irradiating the measurement light to the specimen and receiving the measurement light returning from the specimen; and
the distance measurement unit includes a distance calculation unit that calculates the absolute distance between the tip of the insertion portion and the specimen based on an optical path length from the base light split unit to the specimen, which is calculated using at least the base light and the measurement light reflecting on the specimen as an interference light.

7. The endoscope observation device according to claim 6, wherein:
the distance measurement unit includes:
a low coherence light source;
a reference light split unit that splits a low coherence light emitted from the low coherence light source into a reference light and guides a rest of the coherence light to the insertion portion;
an optical path length adjustment unit that adjusts an optical path length of the reference light split by the reference light split unit; and
an optical coupler that combines the measurement light and the base light returning from the insertion portion with the reference light returning from the optical path length adjustment unit to cause an interference; and
the distance calculation unit calculates the absolute distance between the tip of the insertion portion and the specimen based on a difference between a first optical path length of the reference light at a time point when the measurement light interferes with the reference light in the optical coupler, and a second optical path length of the reference light at a time point when the base light is interfered with the reference light in the optical coupler.

8. The endoscope observation device according to claim 7, wherein the optical path length adjustment unit includes a mirror that reflects the reference light split by the light split unit to return to the optical coupler, and a mirror movement unit that moves the mirror along an optical axis of the reference light.

9. The endoscope observation device according to claim 8, wherein:
the optical path length adjustment unit includes a reference light split unit that splits the reference light into a plurality of lights;
the mirrors and the mirror movement units are disposed to each of the reference lights split by the reference light split unit; and
ranges for adjusting the optical path lengths of the reference lights by the mirror movement units are different.

10. The endoscope observation device according to claim 9, wherein ranges for adjusting the optical path lengths of the reference lights by two or more mirror movement units are sequentially provided.

11. The endoscope observation device according to claim 6, wherein:
the distance calculation unit includes:
a low coherence light source;
a reference light split unit disposed inside the insertion portion for splitting a low coherence light emitted from the low coherence light source into a reference light, and guiding a rest of the low coherence light to the tip of the insertion portion;
an interference light split unit that splits the measurement light, the base light and the reference light into two respective interference optical paths;
an optical path length difference adjustment unit that adjusts an optical path length difference between the two interference optical paths; and
an optical coupler that combines the low coherence light passing through the two interference optical paths to cause the interference; and
the distance calculation unit calculates the absolute distance between the tip end of the insertion portion and the specimen based on a difference between the first optical path length difference between the two interference optical paths at a time point when the measurement light interferes with the reference light in the optical coupler, and a second optical path length difference between the two interference paths at a time point when the base light interferes with the reference light in the optical coupler.

12. The endoscope observation device according to claim 6, wherein:
the distance measurement unit includes:
an interference light split unit that splits the measurement light and the base light into two respective interference optical paths;
an optical path length difference adjustment unit that adjusts an optical path length difference between the two interference optical paths; and
an optical coupler that combines the low coherence light passing through the two interference optical paths; and
the distance calculation unit calculates the absolute distance between the tip of the insertion unit and the specimen based on an optical path length difference between the two interference optical paths at a point when the measurement light interferes with the base light in the optical coupler.

13. The endoscope observation device according to claim 6, wherein the base light split unit comprises a reflective film provided to a tip of the insertion portion to reflect a part of the measurement light.

14. The endoscope observation device according to claim 6, further comprising:
an optical modulator that allows the reference light split by the reference light split unit to be frequency modulated at a different frequency; and
a frequency detector that detects a frequency of the light interfered in the optical coupler.

15. An observation device including a light emitting portion for irradiating a light to a specimen and a light receiving portion that receives an observation light returning from the specimen at its tip for forming an image of the observation light received by the light receiving portion, comprising:

a distance measurement unit that calculates an absolute distance between the tip and the specimen through an interference of a low coherence light;
a correction unit that corrects a piece of brightness information of the observation based on the absolute distance measured by the distance measurement unit;
an image forming unit that forms an image of the specimen based on the brightness information of the observation light corrected by the correction unit; and
an optical element that splits the low coherence light from the observation light.

16. An observation method using an endoscope for forming an image by irradiating a light to a specimen from a tip of an insertion portion to be inserted into a body cavity, and receiving an observation light returning from the specimen, comprising:
a measurement step of measuring an absolute distance between the tip of the insertion portion and the specimen through an interference of a low coherence light;
a correction step of correcting a piece of brightness information of the observation light based on the measured absolute distance;
an image forming step of forming an image of the specimen based on the corrected brightness information of the observation light and
a splitting step of splitting the low coherence light from the observation light.

17. An observation method using an endoscope for forming an image by irradiating a light to a specimen from a tip of an insertion portion to be inserted into a body cavity, and receiving an observation light returning from the specimen, comprising:
a measurement step of measuring an absolute distance between the tip of the insertion portion and the specimen through an interference of a low coherence light;
a correction step of correcting a piece of brightness information of the observation light based on the measured absolute distance; and
an image forming step of forming an image of the specimen based on the corrected brightness information of the observation light;
wherein the measurement step further includes:
splitting a reference light from the low coherence light, and guiding a rest of the coherence light to the insertion portion;
splitting the low coherence light into a base light and a measurement light at a tip of the insertion portion;
irradiating the split measurement light and receiving the measurement light returning from the specimen;
adjusting an optical path length of the split reference light;
combining the measurement light and the reference light returning from the tip of the insertion portion to cause an interference; and
calculating the absolute distance based on a difference between a first optical path length of the reference light at a time point when the interference occurs between the measurement light and the reference light returning from the specimen and a second optical path length of the reference light at a time point when an interference occurs between the base light and the reference light.

18. The observation method using the endoscope according to claim 17, wherein the reference light is split to a plurality of optical paths each having a different optical path length, and each of the split reference lights is subjected to adjustment of the optical path length.

19. The observation method using the endoscope according to claim 18, wherein ranges for adjusting the optical path lengths of the split reference lights are sequentially provided.

20. The observation method using the endoscope according to claim 18, wherein the split reference lights are frequency modulated to different frequencies such that an optical frequency that causes the interference is detected.

* * * * *